(12) United States Patent
Kuehn et al.

(10) Patent No.: US 10,549,993 B2
(45) Date of Patent: Feb. 4, 2020

(54) METHOD FOR GENERATING OXYGEN FROM COMPOSITIONS COMPRISING IONIC LIQUIDS

(71) Applicant: DIEHL AVIATION GILCHING GMBH, Gilching (DE)

(72) Inventors: Fritz Kuehn, Garching (DE); Florian J. Groche, Munich (DE); Christoph Kallfass, Schwaebisch Hall (DE)

(73) Assignee: Diehl Aviation Gilching GmbH, Gilching (DE)

( * ) Notice: Subject to any disclaimer, the term of this patent is extended or adjusted under 35 U.S.C. 154(b) by 90 days.

(21) Appl. No.: 15/815,741

(22) Filed: Nov. 17, 2017

(65) Prior Publication Data

US 2018/0141812 A1    May 24, 2018

(30) Foreign Application Priority Data

Nov. 18, 2016   (EP) .................................... 16199633

(51) Int. Cl.
*C01B 13/02*    (2006.01)
*B01J 31/02*    (2006.01)
(Continued)

(52) U.S. Cl.
CPC ....... *C01B 13/0225* (2013.01); *B01J 31/0281* (2013.01); *B01J 31/0288* (2013.01); *B01J 31/0289* (2013.01); *C01B 15/01* (2013.01); *C01B 15/103* (2013.01); *C01B 15/12* (2013.01); *C01G 3/02* (2013.01); *C01G 21/08* (2013.01);
(Continued)

(58) Field of Classification Search
CPC .................................................. C01B 13/0225
See application file for complete search history.

(56) References Cited

U.S. PATENT DOCUMENTS 2,035,896 A    3/1936   Kerwin
4,548,730 A    10/1985  Koslow
(Continued)

FOREIGN PATENT DOCUMENTS

CN    105776144 A    7/2016
DE      3837432 A1   5/1990
(Continued)

OTHER PUBLICATIONS

European Search Report for Applicaiton No. 16199633.5-1354 dated Feb. 17, 2017, 18 pages.
(Continued)

*Primary Examiner* — Melissa S Swain
(74) *Attorney, Agent, or Firm* — Laurence A. Greenberg; Werner H. Stemer; Ralph E. Locher

(57) ABSTRACT

The present invention is directed to a method for generating oxygen comprising providing at least one oxygen source, providing at least one ionic liquid, providing at least one metal oxide compound, wherein the oxygen source is a peroxide compound, the ionic liquid is in the liquid state at least in the temperature range from −10° C. to +50° C., and the metal oxide compound is an oxide of one single metal or of two or more different metals, said metal(s) being selected from the metals of groups 2 to 14 of the periodic table of the elements, and contacting the oxygen source, the ionic liquid, and the metal oxide compound.

16 Claims, 22 Drawing Sheets

(51) Int. Cl.

| | | |
|---|---|---|
| *C01B 15/01* | (2006.01) | |
| *C01B 15/10* | (2006.01) | |
| *C01B 15/12* | (2006.01) | |
| *C01G 3/02* | (2006.01) | |
| *C01G 21/08* | (2006.01) | |
| *C01G 37/02* | (2006.01) | |
| *C01G 45/02* | (2006.01) | |
| *C01G 51/04* | (2006.01) | |
| *C07D 233/58* | (2006.01) | |
| *C01G 49/00* | (2006.01) | |
| *C01G 53/04* | (2006.01) | |

(52) U.S. Cl.
CPC ............. *C01G 37/02* (2013.01); *C01G 45/02* (2013.01); *C01G 51/04* (2013.01); *C07D 233/58* (2013.01); *C01G 49/009* (2013.01); *C01G 49/0072* (2013.01); *C01G 53/04* (2013.01); *C01P 2002/32* (2013.01); *C01P 2002/34* (2013.01)

(56) References Cited

U.S. PATENT DOCUMENTS

| | | | |
|---|---|---|---|
| 4,963,327 A | | 10/1990 | Russell |
| 7,666,903 B2* | | 2/2010 | Wulff ................ A61K 8/39 514/467 |
| 8,147,760 B1 | | 4/2012 | Huvard et al. |
| 8,455,421 B2* | | 6/2013 | Seddon ................ C11D 3/28 134/40 |
| 2007/0007135 A1 | | 1/2007 | Gheczy et al. |
| 2011/0017209 A1 | | 1/2011 | Monzyk |
| 2011/0073331 A1 | | 3/2011 | Xu |

FOREIGN PATENT DOCUMENTS

| | | |
|---|---|---|
| DE | 19602149 A1 | 7/1997 |
| DE | 102006042320 A1 | 3/2008 |
| DE | 102009041065 A1 | 3/2011 |
| EP | 0306840 A2 | 3/1989 |
| EP | 2856867 A1 | 4/2015 |
| JP | S6177604 A | 4/1986 |
| JP | 61236602 A | 10/1986 |
| JP | S61227903 A | 10/1986 |
| JP | 2009138254 A | 6/2009 |
| WO | 8602063 A1 | 4/1986 |
| WO | 9743210 A1 | 11/1997 |
| WO | 0240397 A1 | 5/2002 |
| WO | 2006083663 A2 | 8/2006 |
| WO | 2013153178 A1 | 10/2013 |

OTHER PUBLICATIONS

European Search Report for Application No. 16199622.8-1354 dated Jan. 30, 2017, 7 pages.
European Search Report for Application No. 16199625.1-1754 dated May 22, 2017, 12 pages.
European Search Report for Application No. 16199630.1-1354, dated Jan. 30, 2017, 7 pages.
European Search Report for Application No. 16199636.8-1354, dated Feb. 17, 2017, 18 Pages.
European Search Report for Application No. 16199637.6-1754 dated May 22, 2017, 12 pages.
European Search Report for Application No. 16199641.8-1754, dated Jun. 8, 2017, 8 pages.
Fluck, et al. "New Notations in the Periodic Table" International Union of Pure and Applied Chemistry Inorganic Chemistry Division, Pure&Appl. Chem., vol. 60, No. 3, pp. 431-436, 1988.
Gaston P. Barreto et al. "Effect of ionic liquid on the termal decomposition of cyclic organic peroxides", Arabian Journal of chemistry, Jun. 1, 2016, 10 pages.
Rakhmanov, et al. "Oxidation of Dibenzothiphene with Hydrogen Peroxide in Ionic Liquids" ISSN 0965-5441, Petroleum Chemistry, 2012, vol. 52, No. 3, pp. 213-214.
Sitze, et al. "Ionic Liquids Based on FeCl3 and FeCl2. Raman Scattering and ab Initio Calculations" Inorg. Chem. 2001, 40, 2298-2304.

* cited by examiner

METHOD FOR GENERATING OXYGEN FROM COMPOSITIONS COMPRISING IONIC LIQUIDS

FOREIGN PRIORITY

This application claims priority to European Patent Application No. 16199633.5 filed Nov. 18, 2016, the entire contents of which is incorporated herein by reference.

TECHNICAL FIELD

The present invention relates to methods for generating oxygen.

BACKGROUND

Humans cannot exist without oxygen. In many environments, however, oxygen supply is insufficient or there is a risk of emergency situations involving a shortage of oxygen, for example in submarines, in mines, in space capsules, and also in air planes. Air pressure decreases with increasing flight altitude, and at cruising altitudes of many aircrafts, in particular long-range aircrafts, sufficient oxygen for human beings is no longer available. Therefore, the aircraft cabins are pressurized in order to ensure sufficient oxygen supply. In case of a sudden de-pressurization of an aircraft cabin, oxygen masks must be available, which supply oxygen to crew and passengers until the aircraft reaches a flight level where sufficient oxygen is available.

The oxygen which is provided by these emergency systems is typically produced by so-called "chlorate candles" or "oxygen candles". These chemical oxygen generators contain chlorates or perchlorates as an oxygen source, as well as various additives such as fuels, catalysts, binders and moderators. Chlorate candles are often in the form of cylindrical rods, i.e. they have a shape similar to candles. Chlorate candles are disclosed, for example, in WO 97/43210.

Known chlorate candles require high temperatures at which the oxygen production takes place. Namely, in chlorate candles oxygen is released at temperatures between 450° C. and 700° C. Therefore, effective heat insulation of chlorate candles is required, resulting in a weight and size penalty. Furthermore, decomposition of chlorates and perchlorates tends to produce toxic side products, in particular chlorine, which must be removed from the oxygen stream, thus additionally adding size and weight. Furthermore, there is a risk of system failure. In chlorate candles the reaction zone is normally liquid, i.e. there is a liquid zone travelling through the candle, starting at the point of ignition. The liquid zone within the otherwise solid candle considerably destabilizes the candle such that mechanical shocks or even slight vibrations may result in separation of the candle portions, thus interrupting the heat transfer and discontinuing the chlorate or perchlorate decomposition. In such a case, oxygen production may be interrupted, although oxygen is still vitally needed.

A different type of chemical oxygen generators uses peroxides as oxygen sources, for example sodium percarbonate, sodium perborate, or a urea adduct of hydrogen peroxide. Decomposition of the peroxides yields oxygen, and the decomposition reaction can be started by contacting the peroxide compounds with an appropriate enzyme or transition metal catalyst. Chemical oxygen generators of this type are disclosed in U.S. Pat. No. 2,035,896, WO 86/02063, JPS 61227903, and DE 196 02 149.

Many known peroxide-based oxygen generators use water for providing contact between the peroxides and the catalysts. Unfortunately, water freezes at 0° C. and, therefore, no oxygen can be produced below 0° C., while some emergency systems must be operational below 0° C. Also, the decomposition of peroxides in aqueous solutions may result in vehement effervescing of the reaction mixture. As a consequence, an oxygen generating device containing a peroxide-based oxygen generating composition must have a complicated structure.

It would be beneficial to provide a solution to at least some of the problems of the prior art outlined above, and to provide a method for generating oxygens which produces breathable oxygen reliably and continuously in a wide temperature range, and preferably including subfreezing temperatures. The oxygen produced should be at a low temperature, preferably below 150° C., and further preferably free from toxic or otherwise noxious components such as chlorine or carbon monoxide. It would be also beneficial to provide a method capable to produce oxygen over an extended period of time and with a significant flow rate.

SUMMARY

Exemplary embodiments of the invention include a method for generating oxygen comprising providing at least one oxygen source, providing at least one ionic liquid, providing at least one metal oxide compound, wherein the oxygen source is a peroxide compound, the ionic liquid is in the liquid state at least in the temperature range from −10° C. to +50° C., and the metal oxide compound is an oxide of one single metal or of two or more different metals, said metal(s) being selected from the metals of groups 2 to 14 of the periodic table of the elements, and contacting the oxygen source, the ionic liquid, and the metal oxide compound.

Exemplary embodiments of the invention are based on an entirely new concept, the use of ionic liquids in chemical oxygen generating compositions.

Technical implementations of this inventive concept include a composition for generating oxygen, a method for generating oxygen from this composition, a device for generating oxygen containing the composition, and the use of an ionic liquid as a dispersant or solvent and/or as a heat sink in the composition and/or for releasing oxygen from the composition over an extended period of time.

Implementations of this inventive concept also include the composition being in the form of a kit, i.e. in a form preventing that all constituents of the composition, which are required for initiating and supporting oxygen generation, can come into physical contact with each other.

Implementations of this invention further include that the kit is specifically adapted for filling or refilling a device for generating oxygen according to this invention.

As can be easily understood, the constituents of the composition are the same, irrespective of which technical implementation of the invention is contemplated. Therefore, any disclosure provided for a particular implementation, such as composition, device, method or use, is analogously applicable to the other implementations of this invention.

Embodiments 1 to 83 below constitute exemplary implementations of this invention.

1. A composition for generating oxygen, comprising
    at least one oxygen source,
    at least one ionic liquid, and
    at least one metal oxide compound, wherein
        the oxygen source comprises a peroxide compound,
        the ionic liquid is in the liquid state at least in a temperature range from −10° C. to +50° C., and
        the metal oxide compound is an oxide of one single metal or of two or more different metals, said metal(s) being selected from the metals of groups 2 to 14 of the periodic table of the elements.

2. The composition according to embodiment 1, wherein the oxygen source and the metal oxide compound, or the oxygen source and the ionic liquid, or the metal oxide compound and the ionic liquid, are not in physical contact with each other.

3. The composition according to embodiment 1 or 2, wherein the oxygen source is selected from alkali metal percarbonates, alkali metal perborates, urea hydrogen peroxide, and mixtures thereof.

4. The composition according to any one of embodiments 1 to 3, wherein the oxygen source is one or more of $Na_2CO_3 \times 1.5\ H_2O_2$, $NaBO_3 \times 4H_2O$, $NaBO_3 \times H_2O$ and urea hydrogen peroxide.

5. The composition according to any one of embodiments 1 to 4, wherein the ionic liquid is at least one salt having a cation and an anion, wherein the cation is selected from the group consisting of imidazolium, pyrrolidinium, ammonium, choline, pyridinium, pyrazolium, piperidinium, phosphonium, and sulfonium cations, and wherein the cation may have at least one substituent.

6. The composition according to any one of embodiments 1 to 5, wherein the ionic liquid is at least one salt having a cation and an anion, wherein the anion is selected from the group consisting of dimethylphosphate, methylsulfate, trifluoromethylsulfonate, bis(trifluoromethylsulfonyl)imide, chloride, bromide, iodide, tetrafluoroborate, and hexafluorophosphate.

7. The composition according to any one of embodiments 1 to 6, wherein the ionic liquid is selected from the group consisting of
butyltrimethylammoniumbis(trifluoromethylsulfonyl) imide ([Me3BuN]TFSI)
1-butyl-3-methylimidazoliumtrifluoromethanesulfonate (BMImOTf),
1-butyl-3-methylimidazoliumdimethylphosphate (BMImPO$_4$Me$_2$),
1-butyl-3-methylimidazoliummethylsulfate (BMImSo$_4$Me),
1,1-butylmethylpyrrolidiniumbis(trifluoromethylsulfon) imide (BmpyrTFSI),
1,3-dimethylimidazoliumdimethylphosphate (MMImPO$_4$Me$_2$),
1,3-dimethylimidazoliummethylsulfate (MMImSO$_4$Me).

8. The composition according to any one of embodiments 1 to 7, wherein the metal oxide compound is at least one oxide containing one single metal, optionally in different oxidation states.

9. The composition according to any one of embodiments 1 to 8, wherein the metal oxide compound is one or more of $MnO_2$, $Co_3O_4$, $CrO_3$, $Ag_2O$, $CuO$, and $PbO_2$.

10. The composition according to any one of embodiments 1 to 9, wherein the metal oxide compound is at least one oxide containing at least two different metals.

11. The composition according to anyone of embodiments 1 to 10, wherein the metal oxide compound is selected from spinel type metal oxides, ilmenite type metal oxides and perovskite type metal oxides.

12. The composition according to anyone of embodiments 1 to 11, wherein the metal oxide compound is selected from mixed cobalt iron oxides, mixed copper iron oxides, mixed nickel iron oxides, mixed manganese iron oxides, mixed copper manganese oxides, mixed cobalt manganese oxides, mixed nickel manganese oxides, mixed nickel cobalt oxides, mixed lanthanum iron nickel oxides, lanthanum strontium manganite, and mixtures thereof.

13. The composition according to any one of embodiments 1 to 12, wherein the metal oxide compound is at least one of $CoFe_2O_4$, $Co_{1.5}Fe_{1.5}O_4$, $Co_2FeO_4$, $CuFe_2O_4$, $Cu_{1.5}Mn_{1.5}O_4$, $Co_2MnO_4$, $NiMnO_3$, $NiCo_2O_4$, $La_{0.5}Sr_{0.5}MnO_3$, and $LaFe_{0.25}Ni_{0.75}O_3$.

14. The composition according to any one of embodiments 1 to 13, wherein the composition is provided as a kit of at least two physically separated components, each component lacking at least one of the oxygen source, the ionic liquid, and the metal oxide compound.

15. The composition according to embodiment 14, wherein one component comprises a metal oxide compound formulation and the ionic liquid formulation, and the other component comprises an oxygen source formulation.

16. The composition according to embodiment 14, wherein one component comprises an oxygen source formulation and a metal oxide compound formulation, and the other component comprises a ionic liquid formulation.

17. The composition according to embodiment 14, wherein the kit comprises a third component, one component comprising an oxygen source formulation, the other component comprising a ionic liquid formulation, and the third component comprising a metal oxide compound formulation.

18. The composition according to any one of embodiments 1 to 17, wherein the oxygen source is present in an amount ranging from 10 to 80 weight % of the composition, the ionic liquid is present in an amount ranging from 20 to 80 weight % of the composition, and the metal oxide compound is present in an amount ranging from more than 0 to 20 weight % of the composition.

19. The composition according to any one of embodiments 1 to 18, wherein at least one of the oxygen source and the metal oxide compound is in the form of powders or is in the form of at least one powder compact.

20. The composition according to embodiment 19, wherein the at least one powder compact has been compacted with a pressure in the range of 1 to 220 MPa.

21. The composition according to any one of embodiments 14 to 20, wherein the kit comprises at least two different metal oxide compounds and/or at least two peroxide compound which differ in degree of compaction.

22. A method for generating oxygen comprising
providing at least one oxygen source,
providing at least one ionic liquid,
providing at least one metal oxide compound, wherein
the oxygen source is a peroxide compound,
the ionic liquid is in the liquid state at least in the temperature range from −10° C. to +50° C., and
the metal oxide compound is an oxide of one single metal or of two or more different metals, said metal(s) being selected from the metals of groups 2 to 14 of the periodic table of the elements, and
contacting the oxygen source, the ionic liquid, and the metal oxide compound.

23. The method according to embodiment 22, wherein the oxygen source and the ionic liquid are provided as a first component, the metal oxide compound is provided as a second component, and the step of contacting comprises mixing the first and the second components.

24. The method according to embodiment 22, wherein the metal oxide compound and the ionic liquid are provided as a first component, the oxygen source is provided as a second component, and the step of contacting comprises mixing the first and the second component.

25. The method according to embodiment 22, wherein the oxygen source and the metal oxide compound are provided as a first component, the ionic liquid is provided as a second component, and the step of contacting comprises mixing the first and the second components.

26. The method according to embodiment 22, wherein the oxygen source is provided as a first component, the ionic liquid is provided as a second component, the metal oxide compound is provided as a third component, and the step of contacting comprises mixing the first, the second, and the third components.

27. The method according to any one of embodiments 22 to 26, wherein the oxygen source is selected from alkali metal percarbonates, alkali metal perborates, urea hydrogen peroxide, and mixtures thereof.

28. The method according to any one of embodiments 22 to 27, wherein the oxygen source is one or more of $Na_2CO_3 \times 1.5\ H_2O_2$, $NaBO_3 \times 4H_2O$, $NaBO_3 \times H_2O$, and urea hydrogen peroxide.

29. The method according to any one of embodiments 22 to 28, wherein the ionic liquid is at least one salt having a cation and an anion, wherein the cation is selected from the group consisting of imidazolium, pyrrolidinium, ammonium, choline, pyridinium, pyrazolium, piperidinium, phosphonium, and sulfonium cations, and wherein the cation may have at least one substituent.

30. The method according to any one of embodiments 22 to 29, wherein the ionic liquid is at least one salt having a cation and an anion, wherein the anion is selected from the group consisting of dimethylphosphate, methylsulfate, trifluoromethylsulfonate, bis(trifluoromethylsulfonyl)imide, chloride, bromide, iodide, tetrafluoroborate, and hexafluorophosphate.

31. The method according to any one of embodiments 22 to 30, wherein the ionic liquid is selected from the group consisting of
butyltrimethylammoniumbis(trifluoromethylsulfonyl)
imide ([Me3BuN]TFSI)
1-butyl-3-methylimidazoliumtrifluoromethanesulfonate (BMImOTO,
1-butyl-3-methylimidazoliumdimethylphosphate ($BMImPO_4Me_2$),
1-butyl-3-methylimidazoliummethylsulfate ($BMImSO_4Me$),
1,1-butylmethylpyrrolidiniumbis(trifluoromethylsulfon) imide (BmpyrTFSI),
1,3-dimethylimidazoliumdimethylphosphate ($MMImPO_4Me_2$),
1,3-dimethylimidazoliummethylsulfate ($MMImSO_4Me$).

32. The method according to any one of embodiments 22 to 31, wherein the metal oxide compound is at least one oxide containing one single metal, optionally in different oxidation states.

33. The method according to any one of embodiments 22 to 32, wherein the metal oxide compound is one or more of $MnO_2$, $Co_3O_4$, $CrO_3$, $Ag_2O$, $CuO$, and $PbO_2$.

34. The method according to any one of embodiments 22 to 33, wherein the metal oxide compound is at least on oxide containing at least two different metals.

35. The method according to any one of embodiments 22 to 34, wherein the metal oxide compound is selected from spinel type metal oxides, ilmenite type metal oxides and perovskite type metal oxides.

36. The method according to any one of embodiments 22 to 35, wherein the metal oxide compound is selected from mixed cobalt iron oxides, mixed copper iron oxides, mixed nickel iron oxides, mixed manganese iron oxides, mixed copper manganese oxides, mixed cobalt manganese oxides, mixed nickel manganese oxides, mixed nickel cobalt oxides, mixed lanthanum iron nickel oxides, mixed lanthanum strontium manganite oxide, and mixtures thereof.

37. The method composition according to any one of embodiments 22 to 36, wherein the metal oxide compound is at least one of $CoFe_2O_4$, $Co1.5Fe1.5O_4$, $Co2FeO_4$, $CuFe_2O_4$, $Cu1.5Mn1.5O_4$, $Co2MnO_4$, $NiMnO_3$, $NiCo_2O_4$, $La0.5Sr0.5MnO_3$, and $LaFe0.25Ni0.75O_3$.

38. The method according to any one of embodiments 22 to 37, wherein at least one of the oxygen source and the metal oxide compound is in the form of powder.

39. The method according to any one of embodiments 22 to 38, wherein at least one of the oxygen source and the metal oxide compound is in the form of at least one powder compact.

40. The method according to embodiment 39, wherein the at least one powder compact has been compacted with a pressure in the range of 1 to 220 MPa.

41. The method according to embodiment 39 or 40, wherein at least one of the oxygen source and the metal oxide compound includes powder compacts having different degrees of compression.

42. The method according to any one of embodiments 22 to 41, wherein the oxygen source and the metal oxide compound are provided as a mixture.

43. The method according to any one of embodiments 22 to 42, wherein the oxygen source is present in an amount ranging from 10 to 80 weight % of the composition, the ionic liquid is present in an amount ranging from 20 to 80 weight % of the composition, and the metal oxide compound is present in an amount ranging from more than 0 to 20 weight % of the composition.

44. A device for generating oxygen comprising
at least one reaction chamber for housing a composition for generating oxygen, the composition comprising a combination of constituents consisting of at least one oxygen source, at least one ionic liquid, and at least one metal oxide compound,
means for maintaining at least one of the oxygen source, the ionic liquid and the metal oxide compound physically separated from the remaining constituents,
means for establishing physical contact of the oxygen source, the ionic liquid and the metal oxide compound, and
means for allowing oxygen to exit the reaction chamber,
wherein the metal oxide compound is an oxide of a single metal or of two or more different metals, said metal(s) being selected from the metals of groups 2 to 14 of the periodic table of the elements, and wherein the oxygen source comprises a peroxide compound.

45. The device according to embodiment 44, wherein the means for allowing oxygen to exit the reaction chamber is selected from a gas permeable membrane, a frit and a molecular sieve.

46. The device according to embodiment 44 or 45, wherein the reaction chamber comprises a first compartment for receiving at least one of the oxygen source, the ionic liquid and the metal oxide compound, and a second compartment for receiving the other constituents.

47. The device according to any one of embodiments 44 to 46, wherein the means for maintaining at least one of the oxygen source, the ionic liquid and the metal oxide compound physically separated comprise at least one receptacle within the chamber for receiving at least one of the oxygen source, the ionic liquid and the metal oxide compound.

48. The device according to any one of embodiments 44 to 47, wherein the means for maintaining at least one of the oxygen source, the ionic liquid and the metal oxide compound physically separated comprise a membrane, a foil, or a glass plate between the first compartment and the second compartment.

49. The device according to any one of embodiments 44 to 48, wherein the means for establishing physical contact comprise a device for destroying the means for maintaining the constituents physically separated, and an activation mechanism for activating the device.

50. The device according to any one of embodiments 44 to 49, wherein the device for destroying is a solid plate, a grid, or a cutting edge.

51. The device according to any one of embodiments 44 to 50, wherein the means for establishing physical contact is a syringe or a dosing mechanism.

52. The device according to any one of embodiments 44 to 51, wherein the at least one reaction chamber is placed within a container having a gas outlet.

53. The device according to any one of embodiments 44 to 52, wherein at least two reaction chambers are placed within a container, the container providing a common gas space for receiving oxygen exiting the reaction chambers.

54. The device according to any one of embodiments 44 to 53, wherein from three to 20 reaction chambers are placed within a container, the container providing a common gas space for receiving oxygen exiting the reaction chambers.

55. The device according to any one of embodiments 44 to 54, wherein the at least one reaction chamber comprises different compositions for generating oxygen.

56. The device according to embodiment 53, wherein at least two reaction chambers comprise different compositions for generating oxygen.

57. The device according to any one of embodiments 52 to 56, wherein the gas outlet comprises means for restricting gas flow.

58. The device according to any one of embodiments 55 to 57, wherein the compositions for generating oxygen differ with respect to the oxygen source and/or with respect to the ionic liquid and/or with respect to the metal oxide compound and/or with respect to degree of compaction of the oxygen source.

59. A charge component for a device for generating oxygen as embodied in any one of embodiments 44 to 58, the charge component comprising an oxygen source formulation and/or an ionic liquid formulation and/or a metal oxide compound formulation, wherein
the oxygen source formulation comprises a peroxide compound,
the ionic liquid formulation is in the liquid state at least in a temperature range from −10° C. to +50° C., and
the metal oxide compound formulation comprises an oxide of one single metal or of two or more different metals, said metal(s) being selected from the metals of groups 2 to 14 of the periodic table of the elements.

60. The charge component according to embodiment 59, wherein the peroxide compound is selected from alkali metal percarbonates, alkali metal perborates, urea hydrogen peroxide, and mixtures thereof.

61. The charge component according to embodiment 59 or 60, wherein the ionic liquid formulation comprises an ionic liquid having a cation and an anion, wherein the cation is selected from the group consisting of imidazolium, pyrrolidinium, ammonium, choline, pyridinium, pyrazolium, piperidinium, phosphonium, and sulfonium cations, and wherein the cation may have at least one substituent, and wherein the anion is selected from the group consisting of dimethylphosphate, methylsulfate, trifluoromethylsulfonate, bis(trifluoromethylsulfonyl)imide, chloride, bromide, iodide, tetrafluoroborate, and hexafluorophosphate.

62. The charge component according to any one of embodiments 59 to 61, wherein the metal oxide compound is one or more of $MnO_2$, $Co_3O_4$, $CrO_3$, $Ag_2O$, $CuO$, and $PbO_2$.

63. The charge component according to any one of embodiments 59 to 62, wherein the metal oxide compound is selected from spinel type metal oxides, ilmenite type metal oxides and perovskite type metal oxides.

64. The charge component according to any one of embodiments 59 to 63, wherein the metal oxide compound is selected from mixed cobalt iron oxides, mixed copper iron oxides, mixed nickel iron oxides, mixed manganese iron oxides, mixed copper manganese oxides, mixed cobalt manganese oxides, mixed nickel manganese oxides, mixed nickel cobalt oxides, and mixed lanthanum iron nickel oxides, mixed lanthanum strontium manganese oxide, and mixtures thereof.

65. The charge component according to any one of embodiments 59 to 64, wherein at least one of the oxygen source formulation and the metal oxide compound formulation is in the form of powders or is in the form of at least one powder compact.

66. Use of an ionic liquid as a dispersant or solvent and as a heat sink in a composition for generating oxygen, the composition further comprising
at least one oxygen source formulation, and
at least one metal oxide compound formulation, wherein
the oxygen source formulation comprises a peroxide compound,
the ionic liquid is in the liquid state at least in a temperature range from −10° C. to +50° C., and
the metal oxide compound formulation comprises a metal oxide compound which is an oxide of one single metal or of two or more different metals, said metal(s) being selected from the metals of groups 2 to 14 of the periodic table of the elements.

67. The use according to embodiment 66, wherein the peroxide compound is selected from alkali metal percarbonates, alkali metal perborates, urea hydrogen peroxide, and mixtures thereof.

68. The use according to embodiment 66 or 67, wherein the peroxide compound is one or more of $Na_2CO_3 \times 1.5\ H_2O_2$, $NaBO_3 \times 4H_2O$, $NaBO_3 \times H_2O$, and urea hydrogen peroxide.

69. The use according to any one of embodiments 66 to 68, wherein the ionic liquid is at least one salt having a cation and an anion, wherein the cation is selected from the group consisting of imidazolium, pyrrolidinium, ammonium, choline, pyridinium, pyrazolium, piperidinium, phosphonium, and sulfonium cations, and wherein the cation may have at least one substituent.

70. The use according to any one of embodiments 66 to 69, wherein the ionic liquid is at least one salt having a cation and an anion, wherein the anion is selected from the group consisting of dimethylphosphate, methylsulfate, trifluoromethylsulfonate, bis(trifluoromethylsulfonyl)imide, chloride, bromide, iodide, tetrafluoroborate, and hexafluorophosphate.

71. The use according to any one of embodiments 66 to 70, wherein the ionic liquid is selected from the group consisting of
butyltrimethylammoniumbis(trifluoromethylsulfonyl) imide ([Me3BuN]TFSI)
1-butyl-3-methylimidazoliumtrifluoromethanesulfonate (BMImOTf), 1-butyl-3-methylimidazoliumdimethylphosphate (BMImPO$_4$Me$_2$),
1-butyl-3-methylimidazoliummethylsulfate (BMImSO$_4$Me),
1,1-butylmethylpyrrolidiniumbis(trifluoromethylsulfonyl)imide (BmpyrTFSI),
1,3-dimethylimidazoliumdimethylphosphate (MMImPO$_4$Me$_2$),
1,3-dimethylimidazoliummethylsulfate (MMImSO$_4$Me).

72. The use according to any one of embodiments 66 to 71, wherein the metal oxide compound is at least one oxide containing one single metal, optionally in different oxidation states.

73. The use according to any one of embodiments 66 to 72, wherein the metal oxide compound is one or more of MnO2, Co3O4, CrO3, Ag2O, CuO, and PbO2.

74. The use according to any one of embodiments 66 to 73, wherein the metal oxide compound is at least one oxide containing at least two different metals.

75. The use according to any one of embodiments 66 to 74, wherein the metal oxide compound is selected from spinel type metal oxides, ilmenite type metal oxides and perovskite type metal oxides.

76. The use according to any one of embodiments 66 to 75, wherein the metal oxide compound is selected from mixed cobalt iron oxides, mixed copper iron oxides, mixed nickel iron oxides, mixed manganese iron oxides, mixed copper manganese oxides, mixed cobalt manganese oxides, mixed nickel manganese oxides, mixed nickel cobalt oxides, mixed lanthanum iron nickel oxides, mixed lanthanum strontium manganese oxide and mixtures thereof.

77. The use according to any one of embodiments 66 to 76, wherein the metal oxide compound is at least one of CoFe2O4, Co1.5Fe1.5O4, Co2FeO4, CuFe2O4, Cu1.5Mn1.5O4, Co2MnO4, NiMnO3, NiCo2O4, and La0.5Sr0.5MnO3.

78. The use according to any one of embodiments 66 to 77, wherein the oxygen source is present in an amount ranging from 10 to 80 weight % of the composition, the ionic liquid is present in an amount ranging from 20 to 80 weight % of the composition, and the metal oxide compound is present in an amount ranging from more than 0 to 20 weight % of the composition.

79. The use according to any one of embodiments 66 to 78, wherein at least one of the oxygen source formulation and the metal oxide compound formulation is in the form of powders or is in the form of at least one powder compact.

80. The use according to embodiment 79, wherein the at least one powder compact has been compacted with a pressure in the range of 1 to 220 MPa.

81. The use according to embodiment 79 or 80, wherein the oxygen source formulation comprises at least two different peroxide compounds and/or at least two peroxide compounds which differ in degree of compaction.

82. The use according to any one of embodiments 79 to 81, wherein the metal oxide compound formulation comprises at least two different metal oxide compounds and/or at least two metal oxide compounds which differ in degree of compaction.

83. Use of an ionic liquid for releasing oxygen from a composition for generating oxygen over an extended period of time, the composition for generating oxygen having the features as defined in any one of embodiments 66 to 82.

A composition, method, device or use for generating oxygen in the sense of this invention is a composition, method, device or use intended for generating oxygen, while any composition, method, device or use which may generate oxygen as a side reaction does not constitute a composition, method, device or use in the sense of this invention.

The oxygen generating compositions according to exemplary embodiments of the invention comprise, as the essential constituents, at least one peroxide compound as an oxygen source, at least one metal oxide compound as a catalyst triggering the oxygen release reaction, and at least one ionic liquid as a carrier for providing contact between the oxygen source and the catalyst, and for dissipating the heat generated during the peroxide decomposition reaction.

The present inventors found that peroxide compounds such as hydrogen peroxide adduct compounds, can be decomposed in ionic liquids by contacting them with metal oxides in a similar manner as in aqueous solution, but without the disadvantages of aqueous solutions. Exemplary composition of this invention do not contain any water. In particular, decomposition of peroxide compounds in ionic liquids yields breathable oxygen at low temperatures, and without requiring bulky thermal insulations for the oxygen generating device.

This can be attributed to the use of ionic liquids as a medium for providing contact between the oxygen source and the catalyst.

Ionic liquids are salts in the liquid state. Therefore, any salt that melts without decomposing or vaporizing yields an ionic liquid. Sometimes, salts which are liquid below the boiling point of water are considered as ionic liquids. Technically interesting are in particular those ionic liquids which are in the liquid state at relatively low temperatures such as at room temperature or even below room temperature.

An ionic compound is considered as an ionic liquid herein when it is in the liquid state at least in a temperature range from −10° C. to +50° C. Preferred ionic liquids are in the liquid state at least from −30° C. to +70° C., and the most preferred ionic liquids are in the liquid state in an even broader temperature range such as from −70° C. to +150° C.

The properties of ionic liquids can be modified and adapted to the particular needs by varying the chemical structure. Typically, ionic liquids are thermally stable, have wide liquid regions, a high heat capacity and nearly no vapour pressure. Most of them are incombustible. They can be even used as flame retardants. Reference is made to US 2011/0073331 A1 disclosing ionic liquid flame retardants, and quoting literature disclosing preparation methods (paragraph 0127).

As indicated above, the ionic liquids used in the present invention should be in the liquid state at a low temperature, preferably down to −30° C. or even below. Such ionic liquids are salts consisting of organic cations and organic or inorganic anions, and both cations and anions are bulky and preferably asymmetric. As a general rule, the melting temperature decreases with increasing bulkiness and decreasing symmetry of cations and anions. Combinations of highly bulky and asymmetric cations and anions may not freeze down to temperatures as low as −120° C. Many ionic liquids are available which are liquid at −70° C. and above.

Suitable cations are, for example, imidazolium, pyrrolidinium, ammonium, choline, pyridinium, pyrazolium, piperidinium, phosphonium, and sulfonium cations. The cations may or may not have substituents. Particularly, the cations may have one or more substituents, for example alkyl side chains such as methyl or butyl side chains. The substitution may be symmetric or asymmetric.

Suitable anions include dimethylphosphate, methylsulfate, trifluoromethylsulfonate, bis(trisfluoromethylsulfonyl) imide, chloride, bromide, iodide, tetrafluoroborate, and hexafluorophosphate. In the case of "small" anions such as chloride, bromide, and iodide, particularly bulky cations can be selected, in order to provide for the desired low temperature liquidity.

Some exemplary ionic liquids are
butyltrimethylammoniumbis(trifluoromethylsulfonyl) imide ([Me3BuN]TFSI)
1-butyl-3-methylimidazoliumtrifluoromethanesulfonate (BMImOTf),
1-butyl-3-methylimidazoliumdimethylphosphate (BMImPO$_4$Me$_2$),
1-butyl-3-methylimidazoliummethylsulfate (BMImSO$_4$Me),
1,1-butylmethylpyrrolidiniumbis(trifluoromethylsulfonyl)imide (BmpyrTFSI),
1,3-dimethylimidazoliumdimethylphosphate (MMImPO$_4$Me$_2$),
1,3-dimethylimidazoliummethylsulfate (MMImSO$_4$Me).

The ionic liquids usable herein are, however, not particularly limited. It is only required that they are liquid and stable (i.e. they do not decompose) in the desired temperature range. Of course, the ionic liquids must not react with any constituents of the oxygen generating composition. The ionic liquids may be used singly or in combinations of two or more. Thus, in exemplary embodiments, this invention uses ionic liquid formulations. Such formulations may contain further additives which do not detrimentally interfere with the peroxide decomposition reaction.

As an oxygen source, peroxide compounds, in particular solid hydrogen peroxide adduct compounds are used. Solid hydrogen peroxide adduct compounds constitute suitable and stable substituents for liquid hydrogen peroxide, are easily storable, long term stable and safe to work with. Exemplary oxygen sources are alkalipercarbonates, e.g. sodium percarbonate (Na2 CO3×1.5H2O2), alkaliperborates, e.g. sodium perborate (NaBO3×4H2O, NaBO3× H2O), and urea hydrogen peroxide (UHP). In UHP urea and hydrogen peroxide are present in a molar ratio of about 1:1.

The peroxide compounds are not particularly limited, as long as they are stable under usual storage conditions, preferably also at elevated temperatures for example in the vicinity of a fire. The peroxide compounds can be soluble or partially soluble or insoluble in the ionic liquids. The peroxide compounds can be used singly or in combinations of two or more; i.e. as oxygen source formulations. Such formulations may contain further additives which do not detrimentally interfere with the peroxide decomposition reaction.

The decomposition reaction of the peroxide compound is catalyzed by metal oxide compounds. Suitable metal oxide compounds are, for example, those which are known to catalyze the decomposition of peroxides in aqueous solutions.

Generally speaking, metal oxide compounds catalyzing peroxide decomposition in compositions comprising ionic liquids, are oxides of one single metal or of two or more different metals. The metal or the metals are selected from the group which consists of the elements of groups 2 to 14 of the periodic table of the elements. The periodic table has 18 groups (see: Pure and Applied chemistry, vol. 60, 3, pages 431-436).

In exemplary embodiments the metal oxide compound is an oxide of one or more metals belonging to the fourth period of the periodic table of the elements. In an alternative embodiment, the metal oxide compound is an oxide comprising, in addition to one or more metals belonging to the fourth period, one or more metal(s) belonging to the second and/or third and/or fifth and/or sixth period(s).

In further exemplary embodiments, the metal oxide compound is an oxide of one or more metals belonging to the fifth and/or sixth period of the periodic table.

In all embodiments, each metal may be present in one single oxidation state or in different oxidation states.

The metal oxide compounds may be used singly or in combinations of two or more different metal oxide compounds, i.e. metal oxide formulations may be used.

Many metal oxide compounds are transition metal oxides. Such transition metal oxides may contain one transition metal, and may as well contain two or more different transition metals. Each transition metal may be present in one single or in different oxidation states. In addition, the transition metal oxides may contain one or more non-transition metals. The transition metal oxides may be used singly or in combinations of two or more different transition metal oxides.

Exemplary transition metal oxide catalysts include oxides of manganese, cobalt, chromium, silver and copper, and mixed oxides of iron and another transition metal such as cobalt, copper, nickel, or manganese, mixed oxides of manganese and another transition metal such as cobalt, nickel, or copper, and mixed oxides containing nickel and cobalt.

As regards structural types, spinel type oxides, ilmenite type oxides, and perovskite type oxides may be specifically mentioned.

As exemplary compounds catalyzing the peroxide decomposition reaction may be mentioned: manganese (IV) oxide (MnO2), cobalt (II, III) oxide (Co3O4), chromium (VI) oxide (CrO3), silver (I) oxide (Ag2O), and copper (II) oxide (CuO), as well as spinel type mixed metal oxides like cobalt iron oxide (CoxFe3-xO4, with 0≤x≤3), such as CoFe2O4, Co1.5Fe1.5O4, and Co2FeO4, copper iron oxide (CuxFe3-xO4, with 0≤x≤3), such as CuFe2O4, nickel iron oxides (NixFe3-xO4, with 0≤x≤3), manganese iron oxides (MnxFe3-xO4, with 0≤x≤3), copper manganese oxides such as Cu1.5Mn1.5O4, cobalt manganese oxides such as Co2MnO4, nickel cobalt oxides such as NiCo2O4, as well as ilmenite type oxides like nickel manganese oxides such as NiMnO3 or oxides containing more than two transition metals, for example LaFexNi1-xO3, with 0≤x≤1, or LaxSr1-xMnO3 with 0≤x≤1.

Transition metals as understood herein are those elements which have an incomplete d-shell, or which may form ions having an incomplete d-shell, including lanthanides and actinides. It goes without saying that only oxides may be used which undergo a redox reaction with hydrogenperoxide. Zincoxide, for example, may not be used, although zinc constitutes a transition metal. It is, however, stressed that the metal oxide compounds are not limited to transition metal oxides. Rather, the metal oxide compounds may be oxides of main group metals, such as PbO2, or oxides of main group metals and transition metals in combination, such as La0.5 Sr0.5MnO3.

The compositions for generating oxygen may comprise from about 10 to 80 weight % of one or more oxygen sources, from about 20 to 80 weight % of one or more ionic liquids, and from more than 0 up to about 20 weight % of one or more metal oxide catalysts. In exemplary embodiments, the oxygen source or mixture of oxygen sources constitutes from 50 to 70 weight %, the ionic liquid or mixture of ionic liquids constitutes from 30 to 60 weight %, and the metal oxide catalyst or mixture of metal oxide catalysts constitutes from more than 0 up to about 10 weight % of the composition. In some embodiments, the oxygen source may constitute up to 98 weight % of the composition, with the amounts of ionic liquid and catalyst being present in amounts as low as about 1% by weight, each. Optionally, further constituents may be present, for example silicon dioxide (as a heat sink), resorcinol (as a radical scavenger), 2-methylhydrochinone, eugenol, phenol, and 4-propylphenol, all of which reduce the peroxide decomposition rate. In some embodiments, the amounts of such additional constituents do not exceed about 20 weight % of the composition. All constituents together add up to 100 weight %.

In the context herein, the term "composition" includes conditions wherein all constituents of the composition are mixed, i.e. are in contact with each other, as well as conditions wherein the constituents are not in contact with each other, or wherein at least not all constituents are in contact with each other. It must be considered that a mixture comprising an ionic liquid, a peroxide compound dissolved or dispersed therein, and a metal oxide catalyst, is not stable. Rather, the decomposition of the peroxide compound starts as soon as the metal oxide catalyst comes into contact with the peroxide compound, in the ionic liquid, or at least shortly thereafter. Therefore, the constituents of the composition for generating oxygen must be stored in a condition wherein the catalyst cannot trigger the release of oxygen from the peroxide compound. This can be achieved by providing the composition for generating oxygen in the form of a "kit of parts", i.e. as a combination of at least two components, the two components comprising the at least one oxygen source, the at least one ionic liquid, and the at least one metal oxide compound. In the at least two components, at least one of the three constituents (the oxygen source(s), the ionic liquid(s), and the metal oxide compound(s)) is not in contact with the other constituents of the composition for generating oxygen.

According to a first embodiment, the composition comprises a first component and a second component, the first component comprising the oxygen source and the ionic liquid, and the second component comprising the metal oxide.

According to a second embodiment, the composition comprises a first component and a second component, the first component comprising the metal oxide and the ionic liquid, and the second component comprising the oxygen source.

According to a third embodiment, the composition comprises a first component and a second component, the first component comprising the oxygen source and the metal oxide, and the second component comprising the ionic liquid.

According to a fourth embodiment, the composition comprises three components, the first component comprising the oxygen source, the second component comprising the ionic liquid, and the third component comprising the transition metal oxide.

Accordingly, an exemplary method for generating oxygen comprises providing at least one oxygen source, providing at least one ionic liquid, providing at least one metal oxide compound, wherein the oxygen source is a peroxide compound, the ionic liquid is in the liquid state at least in the temperature range from −10° C. to +50° C., the metal oxide compound is an oxide of one single metal or of two or more different metals, said metal(s) being selected from the metals of groups 2 to 14 of the periodic table of the elements, and contacting the at least one oxygen source, the at least one ionic liquid, and the at least one metal oxide compound.

According to a first embodiment, the oxygen source and the ionic liquid are provided as a first component, the metal oxide compound is provided as a second component, and the step of contacting comprises mixing the first component and the second component.

According to a second embodiment, the metal oxide compound and the ionic liquid are provided as a first component, the oxygen source is provided as a second component, and the step of contacting comprises mixing the first component and the second component.

According to a third embodiment, the oxygen source and the metal oxide compound are provided as a first component, and the ionic liquid is provided as a second component, and the step of contacting comprises mixing the first component and the second component.

According to a fourth embodiment, the oxygen source is provided as a first component, the ionic liquid is provided as a second component, the metal oxide compound is provided as a third component, and the step of contacting comprises mixing the first component, the second component and the third component.

When the oxygen source and the metal oxide compound are provided as one single component, i.e. in an admixed state, both the oxygen source and the metal oxide compound should be thoroughly dried before mixing. Otherwise, the oxygen source will be decomposed inadvertently. In the absence of any mediator, for example water or an ionic liquid, the solid oxygen source and the solid metal oxide compound constitute long term stable mixtures.

An exemplary device for generating oxygen by the above method is specifically adapted for housing the components of the composition for generating oxygen in a physically separated state, and bringing them into physical contact once generation of oxygen is desired.

An exemplary device comprises at least one reaction chamber. The reaction chamber may have one single compartment or two compartments separated from one another by a membrane or another means which can be easily destroyed, for example a thin glass plate or a thin metal or plastic foil. Alternatively, the reaction chamber may contain at least one receptacle for receiving one or two of the essential constituents of the composition for generating oxygen, i.e. one or two of the at least one oxygen source, the at least one ionic liquid, and the at least one metal oxide compound. By placing at least one of the constituents in a sealable receptacle, while the other constituents are outside the receptacle, or alternatively, by placing at least one of the constituents of the composition for generating oxygen in a first compartment of the reaction chamber, while the other constituents are placed in a second compartment of the reaction chamber, the constituents are maintained physically separated, and a decomposition reaction of the peroxide compound is prevented.

In order to allow the generation of oxygen, physical contact of the constituents of the composition for generating oxygen must be established. This can be achieved, for example, by destroying the membrane or foil or other means separating the first compartment and the second compartment of the reaction chamber, or by destroying the receptacle containing at least one of the constituents of the composition for generating oxygen. The membrane or other separating means may be, for example, destroyed by a cutting edge of a cutting device arranged in one of the compartments of the reaction chamber, and the receptacle arranged within a reaction chamber containing only one compartment may be, for example, destroyed by a solid plate, a grid, or a firing pin. Both the cutting device having the cutting edge and the solid plate or grid are moved upon activation by an actuator, for example a spring mechanism.

The actuator may be actuated, for example, by a person requiring oxygen or may be actuated automatically, once a low oxygen condition is sensed by an oxygen sensor.

Once contact of the constituents has been established, oxygen generation begins promptly or somewhat delayed, depending on the state of the constituents as will be described below. The oxygen leaves the reaction chamber via means allowing the passage of oxygen, while otherwise sealing the reaction chamber, for example a gas permeable membrane, or any other structure which is gas permeable, but liquid tight, e.g. a frit or a molecular sieve. When the reaction chamber is arranged within a container, the oxygen may be released into a head space of the container, and leave the container through an oxygen outlet.

In an exemplary embodiment, the device for generating oxygen comprises more than one reaction chamber, and the at least two reaction chambers are arranged within a common container. Each reaction chamber may be provided, individually, with means for establishing physical contact of the constituents of the composition for generating oxygen, or alternatively, a common such means may be provided for a plurality of the reaction chambers or for all reaction chambers. The oxygen generated in each reaction chamber is released into a common head space of the container, and leaves the container through an oxygen outlet.

The embodiment comprising a plurality of reaction chambers allows that oxygen can be provided over a particularly long time period by charging the reaction chambers with compositions for generating oxygen having different oxygen release profiles. Alternatively, such compositions having different oxygen release profiles may be also charged into one single reaction chamber, thus providing oxygen over a long time period. It is readily apparent that such device for generating oxygen having only one reaction chamber is of a very simple construction. Simple constructions are typically the most reliable ones.

It has been found by the present inventors, that the course of the decomposition reaction of the peroxide compound can be influenced by various factors.

The nature of the peroxide compound has no or almost no influence, i.e. all tested peroxide compounds have been found to behave equivalently. The nature of the ionic liquid has been found to have some influence on the time point of onset of the reaction and on the reaction rate. This influence is due to solubility differences of the oxygen source in the ionic liquid. The decomposition reaction proceeds faster in case of an oxygen source which is highly soluble in the ionic liquid than in the case of an oxygen source having poor or no solubility in the ionic liquid.

The amount of metal oxide catalyst has more influence on the peroxide decomposition reaction. The reaction profile of the decomposition reaction depends on the concentration of the metal oxide catalyst, i.e. the reaction rate, the time point of onset of the reaction, and the reaction temperature is different for different metal oxide catalyst concentrations. The decomposition reaction rate increases with increasing amount of catalyst.

What has the greatest influence on the decomposition reaction profile, is the surface area of the peroxide compound exposed to the metal oxide catalyst. The reaction rate can be considerably varied by reducing or enlarging the surface area of peroxide compound. The reaction is particularly fast, when the peroxo compounds are present in the form of fine particles. Small particles can be easily and quickly dissolved in the ionic liquid, and even in the case of low solubility in the ionic liquid, small particles have a relatively larger surface area than an equal weight of coarser particles.

If it is desired to extend the time span of oxygen generation, or if it is desired to delay the onset of the decomposition reaction, the peroxide compound may be compressed into powder compacts. Powder compacts may differ in shape (having, for example, cylindrical or rectangular block shapes), in dimensions, in degree of compaction (which increases with increasing compaction pressure), and in weight. It has been found that the weight directly influences the amount of oxygen generated, i.e. the reaction is scalable. The reaction rate, however, is independent of the weight and the shape of the powder compacts and also quite independent of the dimensions of the powder compacts.

A strong influence has been found for the degree of compaction. High compaction pressures clearly delayed the onset of the reaction and/or extended the time period of oxygen generation. The reason is that high compaction pressure results in high density of the powder compacts, resulting in low porosity of the powder compacts. Powder compacts having many open pores at the surfaces thereof can be easily and quickly penetrated by the ionic liquid, while powder compacts having only few open pores at the surfaces thereof do not allow fast penetration of the ionic liquid into the bulk of the powder compact. Therefore, contact with the metal oxide catalyst is delayed in the case of powder compacts having a high degree of compaction, and the delay increases with increasing degree of compaction.

In exemplary embodiments, the ionic liquids described above are used as dispersants or solvents and as heat sinks in the compositions for generating oxygen described above.

The disclosed uses, methods and devices may take advantage of any of the materials described above in relation to compositions and vice versa.

All references herein to "comprising" should be understood to encompass "including" and "containing" as well as "consisting of" and "consisting essentially of".

The term "a" means "at least one".

BRIEF DESCRIPTION OF THE DRAWINGS

The invention will be further illustrated by the following non limiting examples with reference to the accompanying drawings, wherein.

DETAILED DESCRIPTION

In all graphs illustrating oxygen evolution or reaction temperature, oxygen evolution (or reaction temperature, respectively) is plotted against runtime, wherein runtime is the time which starts running at the time point of contacting the oxygen source (formulation) and the ionic liquid (formulation) comprising an active ionic liquid.

EXAMPLE 1

Figure 1:
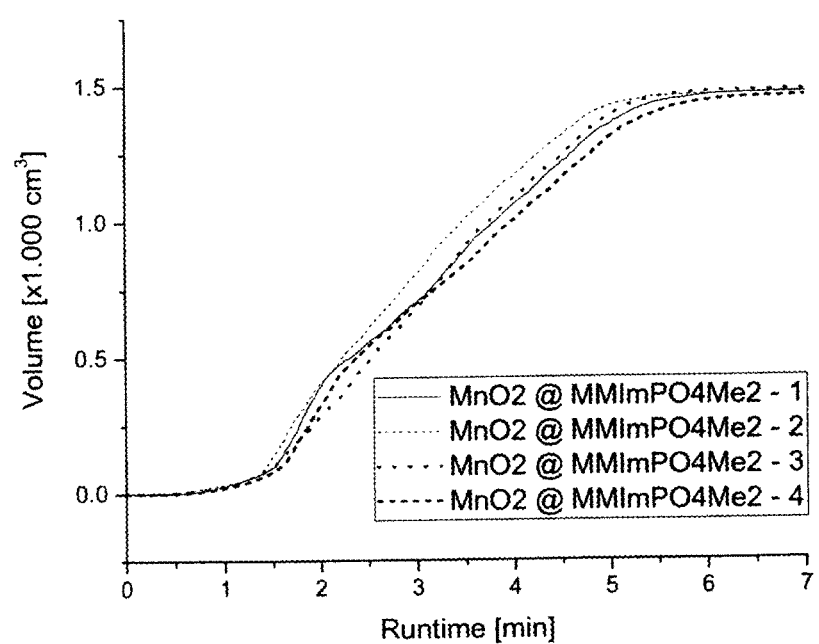
FIG. 1 is a graph illustrating reproducibility of oxygen release from a composition of the present invention.

10.0 g urea hydrogen peroxide adduct (UHP) were added to a dispersion of mol % (relative to UHP) $MnO_2$ (0.184 g) in 5.0 g 1,3-dimethylimidazoliumdimethylphosphate ($MMImPO_4Me_2$), contained in a glass flask. The flask was closed, and the oxygen volume released by the decomposition reaction was measured with a drum gas meter. The experiment was repeated three times. As FIG. 1 shows, the reaction profile was substantially identical in all experiments, proving that the decomposition reaction was reliably reproducible.

EXAMPLE 2

Urea hydrogen peroxide (UHP) adduct in the amounts listed in table 1 was added to dispersions of 2 mol % (relative to UHP) MnO2 in MMImPO4Me2 (amounts listed in table 1) contained in a glass flask. The flask was closed, and the oxygen volume released by the decomposition reaction was measured with a drum gas meter. In addition, the reaction temperature was measured. The results are illustrated in FIGS. 2 and 3.

Figure 2:
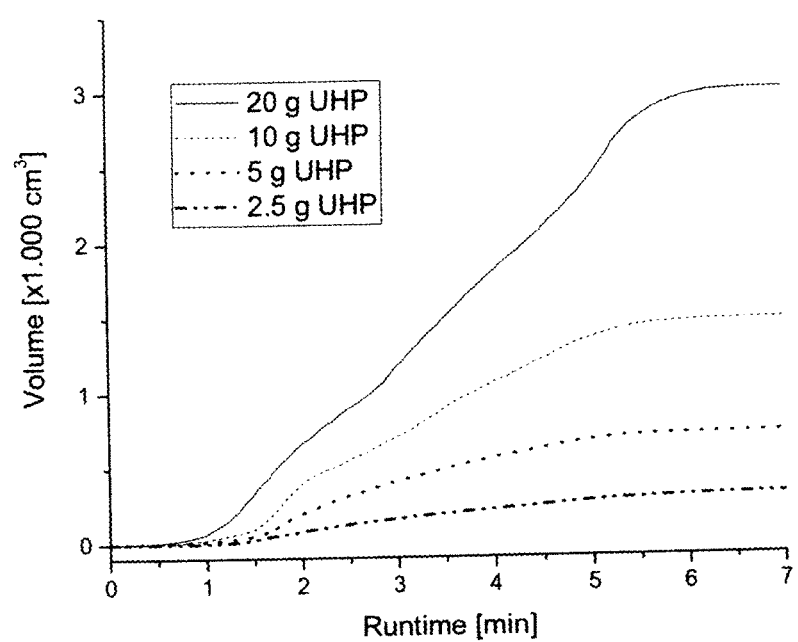
FIG. 2 is a graph illustrating oxygen release from different amounts of UHP through metal oxides in MMImPO4Me2.

FIG. 2 shows that when varying amounts of peroxide compound are added to equivalently varying amounts of ionic liquid and catalyst, the amount of oxygen released by the decomposition reaction increases proportionally, thus proving that the decomposition reaction is scalable for different sizes of devices for generating oxygen.

Figure 3:
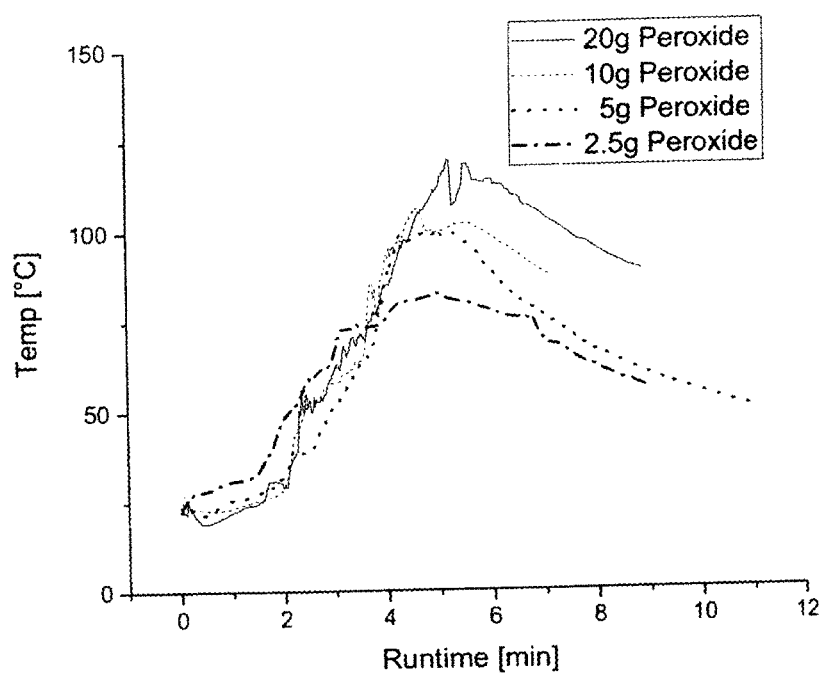
FIG. 3 is a graph illustrating reaction temperatures for the decomposition reactions illustrated in FIG. 2, FIGS. 4*a*, 4*b* are graphs illustrating oxygen release from 1 g UHP in different ionic liquids by catalytic amounts of manganese (IV) dioxide.

FIG. 3 shows that the reaction temperatures increase with increasing amounts of reaction mixture, but remain well below 150° C. even for the sample containing 20 g UHP.

TABLE 1

| peroxide adduct | mass peroxide adduct | mass IL | mass MnO2 catalyst | volume | reaction time |
| --- | --- | --- | --- | --- | --- |
| UHP | 2.5 g | 1.25 g | 0.046 g | 300 cm³ | 6.1 min |
| UHP | 5 g | 2.5 g | 0.092 g | 700 cm³ | 5.9 min |
| UHP | 10 g | 5 g | 0.184 g | 1455 cm³ | 5.9 min |
| UHP | 20 g | 10 g | 0.368 g | 2970 cm³ | 6.1 min |

EXAMPLE 3

Figure 4A:
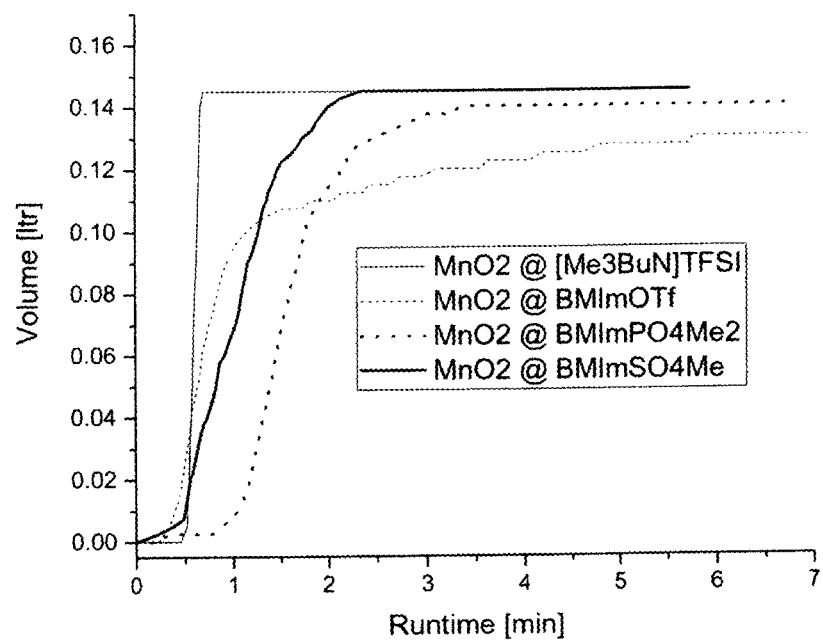
Figure 4B:
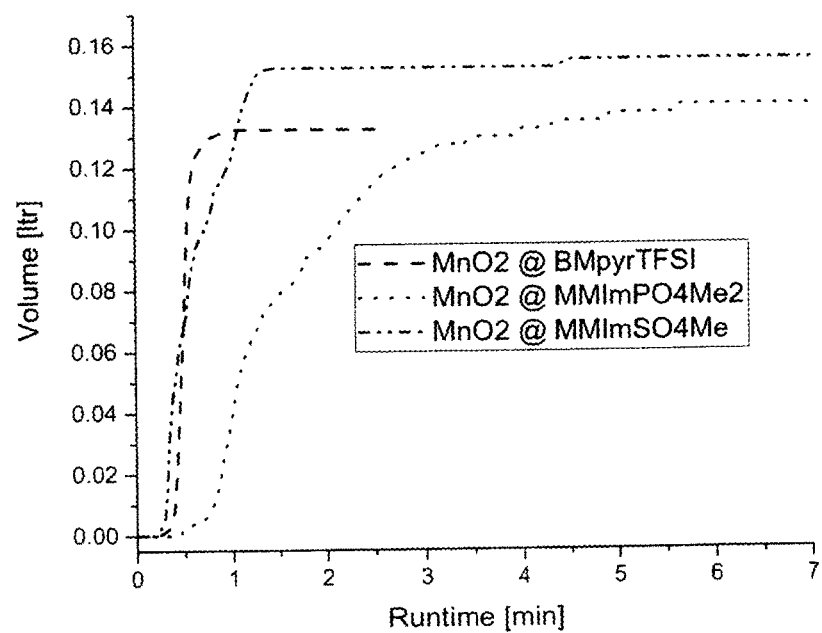

1.0 g urea hydrogen peroxide adduct compound (UHP) was added to a dispersion of 5 mol % (relative to UHP) MnO2 catalyst in 0.5 g of different ionic liquids (IL) contained in a glass flask each. The ionic liquids used are listed below. The flask was closed, and the oxygen volume released by the decomposition reaction was measured with a drum gas meter. The results are shown in FIGS. 4a and 4b. FIGS. 4a and 4b reveal that all ionic liquids worked well. The reaction speed is influenced to some extent by the particular ionic liquid used.

Ionic Liquids:
butyltrimethylammoniumbis(trifluoromethylsulfonyl) imide ([Me3BuN]TFSI)
1-butyl-3-methylimidazoliumtrifluoromethanesulfonate (BMImOTf),
1-butyl-3-methylimidazoliumdimethylphosphate ($BMImPO_4Me_2$),
1-butyl-3-methylimidazoliummethylsulfate ($BMImSO_4Me$),
1,1-butylmethylpyrrolidiniumbis(trifluoromethylsulfonyl)imide (BmpyrTFSI),
1,3-dimethylimidazoliumdimethylphosphate ($MMImPO_4Me_2$),
1,3-dimethylimidazoliummethylsulfate ($MMImSO_4Me$).

EXAMPLE 4

1.0 g urea hydrogen peroxide adduct compound were added to dispersions of different metal oxide catalysts in 0.5 g MMImPO4Me2 contained in a glass flask. The flask was closed, and the oxygen volume released by the decomposition reaction was measured with a drum gas meter. The catalysts used are listed in table 2, and the reaction profiles are shown in FIG. 5.

Figure 5:
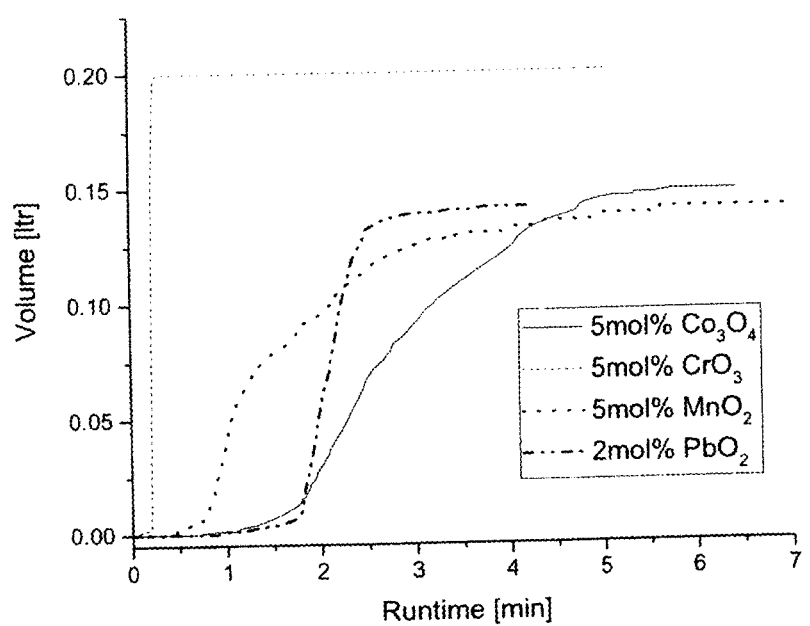
FIG. 5 is a graph illustrating oxygen release from 1 g UHP in MMImPO4Me2 by different metal oxides.

FIG. 5 reveals that both the onset of the reaction and the reaction velocity depend on the particular catalyst used. While in the case of CrO3 the reaction starts immediately after contacting peroxide compound and catalyst, and is finished within a few seconds, in the case of the other catalysts, the onset of the reaction is somewhat delayed, and the reaction velocity is slower.

TABLE 2

| peroxide adduct | metal oxide catalyst | mass catalyst | volume |
| --- | --- | --- | --- |
| UHP | $Co_3O_4$ | 0.128 g | 145 cm³ |
| UHP | $CrO_3$ | 0.053 g | 200 cm³ |
| UHP | $MnO_2$ | 0.092 g | 140 cm³ |
| UHP | $PbO_2$ | 0.051 g | 142 cm³ |
| UHP | $Fe_3O_4$ | 0.123 g | 18 cm³ |

EXAMPLE 5

10.0 g UHP were added to dispersions of different amounts of MnO2 catalyst in 7.5 g $MMImPO_4Me_2$ contained in a glass flask. The amounts and concentrations (relative to UHP) of MnO$_2$ are indicated in table 3. The flask was closed, and the oxygen volume released by the decomposition reaction was measured with a drum gas meter. The reaction profiles are shown in FIG. 6.

Figure 6:
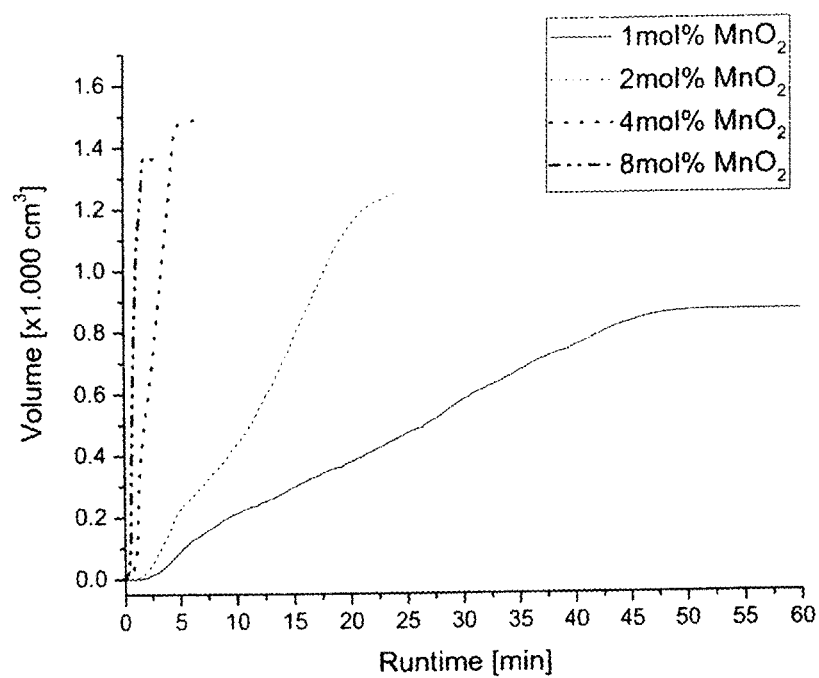
FIG. 6 is a graph illustrating oxygen evolution from 10 g UHP using different catalyst concentrations.

It is evident from FIG. 6 that the catalyst concentration can be varied over a broad range, and that it exerts a strong influence both on the reaction velocity and on the amount of oxygen released. The reaction velocity dramatically increases with increasing catalyst concentration.

TABLE 3

| peroxide adduct | catalyst concentration | mass catalyst | volume | Time1) |
|---|---|---|---|---|
| UHP | 1 mole % | 0.092 g | 863 cm$^3$ | 55.0 min |
| UHP | 2 mole % | 0.184 g | 1253 cm$^3$ | 24.6 min |
| UHP | 4 mole % | 0.368 g | 1488 cm$^3$ | 5.7 min |
| UHP | 8 mole % | 0.736 g | 1365 cm$^3$ | 2.0 min |

1)"time" means time until complete release of all available oxygen

EXAMPLE 6

Urea hydrogen peroxide (UHP), sodiumpercabonate (SPC), and mixtures thereof in the amounts listed in table 4 were added to dispersions of 2 mol % (relative to the peroxide compound) MnO$_2$ in 5.0 g MMImPO$_4$Me$_2$. The reaction vessel was closed, and the oxygen volume released by the decomposition reaction was measured with a drum gas meter. The results are illustrated in FIG. 7.

Figure 7:
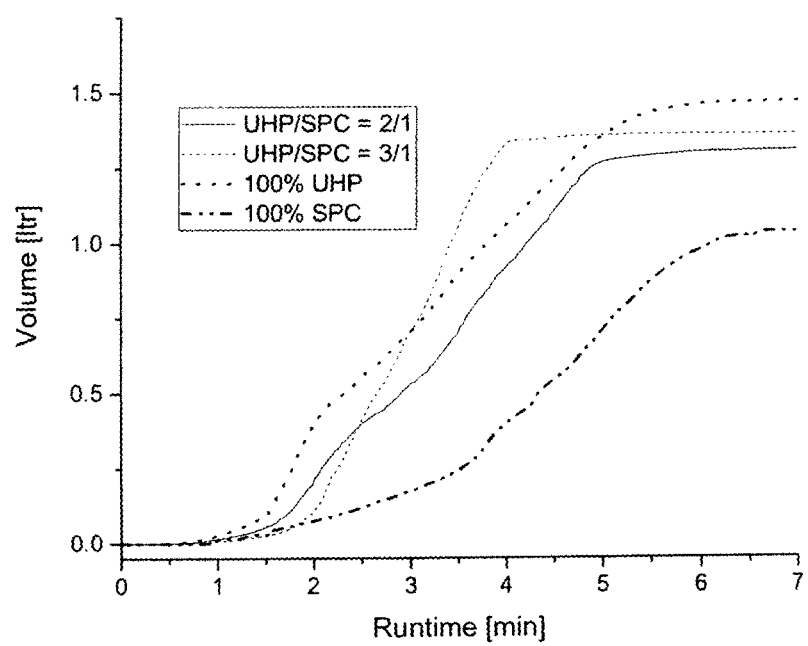
FIG. 7 is a graph illustrating oxygen release from mixtures of SPC and UHP in ionic liquids.

FIG. 7 illustrates that the nature of the peroxide compound has only little influence on the course of the decomposition reaction. The somewhat longer reaction time and reduced oxygen generation can be attributed to the somewhat lower solubility of SPC, as compared to UHP, in the particular ionic liquid used in this experiment.

TABLE 4

| mass UHP | mass SPC | mass MnO$_2$ | volume | time |
|---|---|---|---|---|
| 10 g | 0 | 0.184 g | 1458 cm$^3$ | 5.97 min |
| 7.5 g | 4.2 g | 0.184 g | 1343 cm$^3$ | 5.53 min |
| 6.7 g | 5.4 g | 0.184 g | 1290 cm$^3$ | 4.07 min |
| 0 | 10 g | 0.11 g | 1005 cm$^3$ | 6.60 min |

EXAMPLE 7

2 g urea hydrogen peroxide adduct (UHP) were added to dispersions of 5 mol % (relative to UHP) of different mixed metal oxide catalysts in 1.0 g MMImPO$_4$Me$_2$ contained in a glass flask. The flask was closed, and the oxygen volume released by the decomposition reaction was measured with a drum gas meter. All catalysts were mixed cobalt iron oxides, as listed in table 5. The reaction profiles are shown in FIG. 8.

Figure 8:
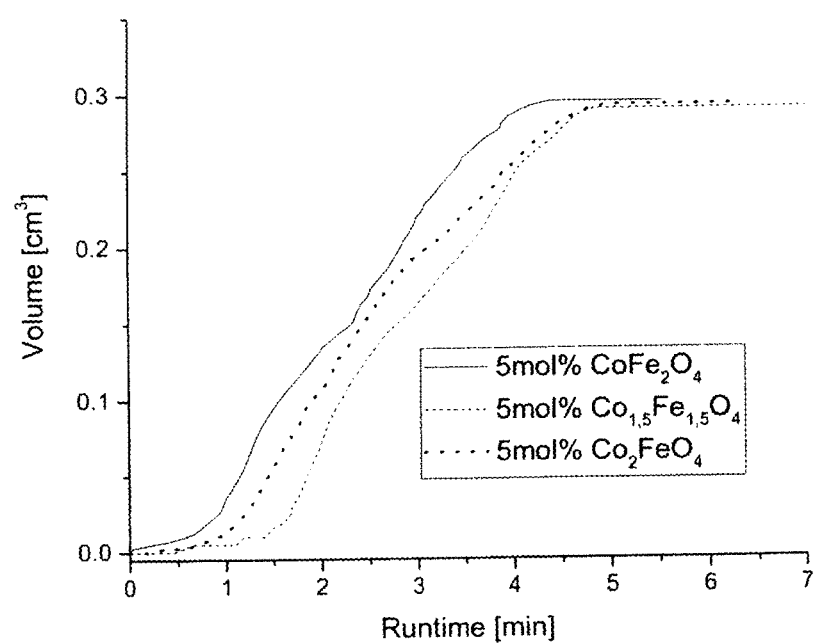
FIG. 8 is a graph illustrating oxygen release from 1 g UHP in MMImPO4Me2 by different metal oxides.

FIG. 8 reveals that all tested cobalt iron oxide catalysts behaved very similar. There was almost no difference in reaction velocity, time point of onset of the reaction, and oxygen volume generated.

TABLE 5

| peroxide adduct | metal oxide | mass catalyst | volume |
|---|---|---|---|
| UHP | CoFe$_2$O$_4$ | 0.249 g | 295 cm$^3$ |
| UHP | Co$_{1.5}$Fe$_{1.5}$O$_4$ | 0.251 g | 290 cm$^3$ |
| UHP | Co$_2$FeO$_4$ | 0.253 g | 290 cm$^3$ |

EXAMPLE 8

Figure 9:
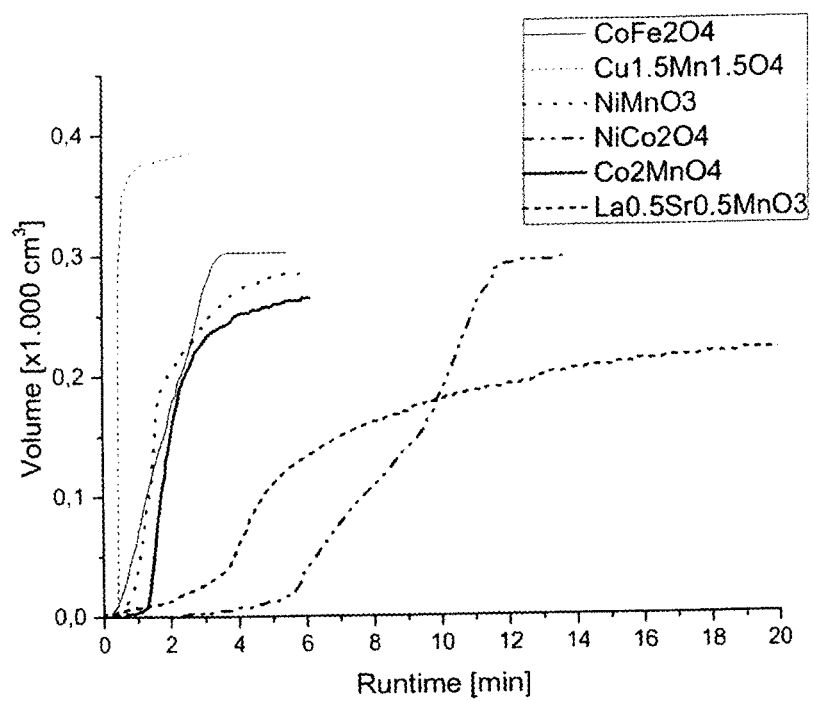
FIG. 9 is a graph illustrating oxygen release from 2 g UHP using different catalysts.

2 g urea hydrogen peroxide adduct (UHP) were added to dispersions of 5 mol % (relative to UHP) of different mixed metal oxide catalysts in 1 g MMImPO4Me2 contained in glass flasks. The flasks were closed, and the oxygen volume released by the decomposition reactions was measured with a drum gas meter. The particular catalyst used are listed in table 6, and the reaction profiles are shown in FIG. 9.

In this example, in contrast to the results obtained in example 7, differences were found between the individual mixed metal oxide catalysts. While not wishing to be bound by this theory, it is believed that the different findings in example 7 and example 8 can be attributed to the fact that the mixed metal oxide catalysts used in example 7 contained the same transition metals, and only the relative amounts were varied, while the mixed metal oxide catalysts used in example 8 contained different transition metals, i.e. each mixed metal oxide contained a different combination of transition metals.

TABLE 6

| catalyst | catalyst mass | volume |
|---|---|---|
| CuFe$_2$O$_4$ | 0.254 g | 243 cm$^3$ |
| Cu$_{1.5}$Mn$_{1.5}$MnO$_4$ | 0.315 g | 385 cm$^3$ |
| NiMnO$_3$ | 0.172 g | 285 cm$^3$ |
| NiCo$_2$O$_4$ | 0.256 g | 295 cm$^3$ |
| Co$_2$MnO$_4$ | 0.252 g | 265 cm$^3$ |
| La$_{0.5}$Sr$_{0.5}$MnO$_3$ | 0.125 g | 223 cm$^3$ |
| LaFe$_{0.25}$Ni$_{0.75}$O$_3$ | 0.245 g | 45 cm$^3$ |

EXAMPLE 9

Urea hydrogen peroxide adduct compound in the amounts listed in table 7 were added to dispersions of 2 mol % (relative to UHP) Co1.5Fe1.5O4 in corresponding amounts (see table 7) of MMImPO4Me2 contained in glass flasks. The flasks were sealed, and the oxygen volume released by the decomposition reaction was measured with a drum gas meter. In addition, the reaction temperatures were measured. The results are illustrated in FIGS. 10 and 11.

Figure 10:
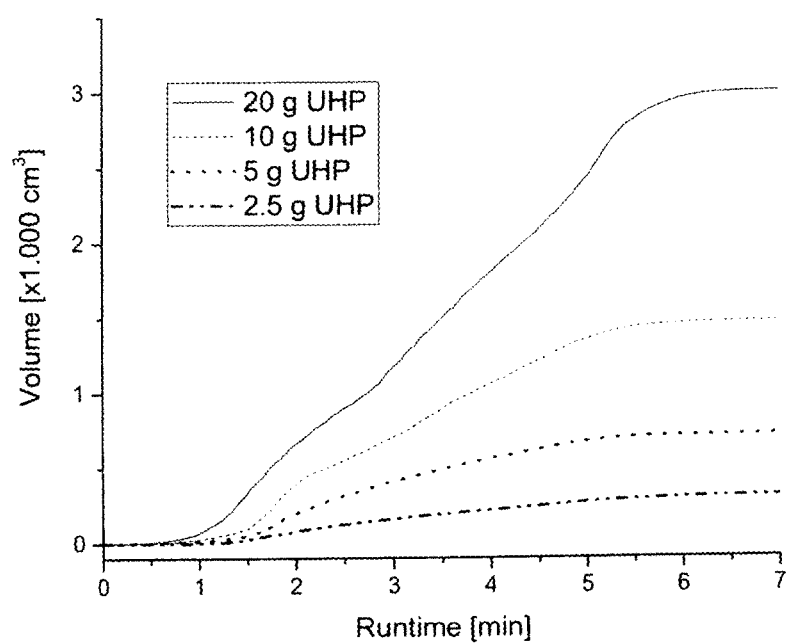
FIG. 10 is a graph illustrating oxygen release from different amounts of UHP through a mixed metal oxide in MMImPO4Me2.

FIG. 10 shows that when varying amounts of peroxide compound are added to equivalently varying amounts of ionic liquid and mixed metal oxide catalyst, the amount of oxygen released increases proportionally, thus proving that the decomposition reaction is scalable for different sizes of devices for generating oxygen.

Figure 11:
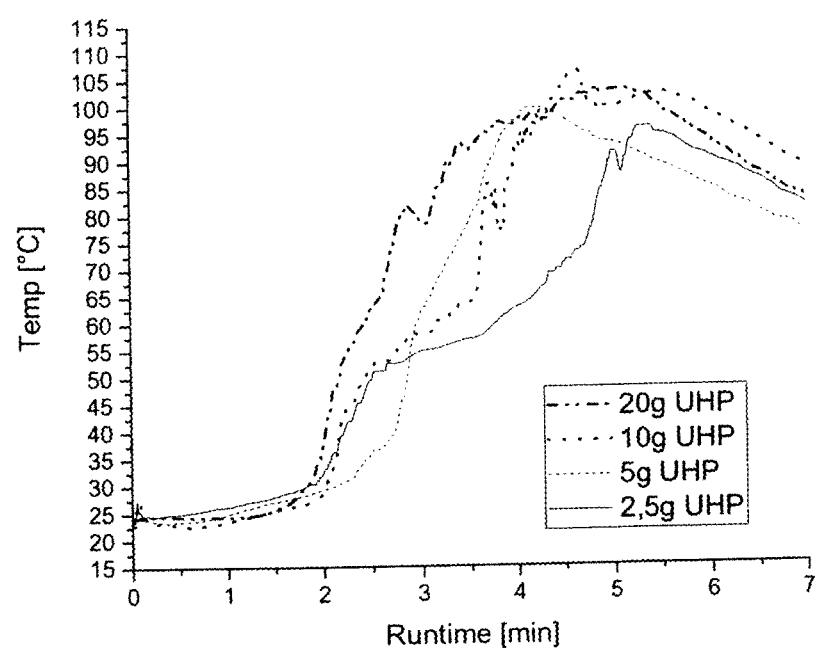
FIG. 11 is a graph illustrating reaction temperatures of the decomposition reactions illustrated in FIG. 10.

FIG. 11 shows that the reaction temperatures increase with increasing amounts of the reaction mixtures. However, the reaction temperatures always remained below 110° C. In the case of example 2 wherein manganese (IV) oxide was used as a catalyst, i.e. an oxide containing only one single transition metal rather than mixed metals, was used as a catalyst, the maximum reaction temperatures appeared to be somewhat higher, thus suggesting a tendency towards lower reaction temperatures with mixed metal oxide catalysts than with single metal oxide catalysts.

TABLE 7

| peroxide adduct | mass peroxide | mass IL | mass catalyst | volume | time |
|---|---|---|---|---|---|
| UHP | 2.5 g | 1.25 g | 0.046 g | 300 cm$^3$ | 6.1 min |
| UHP | 5 g | 2.5 g | 0.092 g | 700 cm$^3$ | 5.9 min |
| UHP | 10 g | 5 g | 0.184 g | 1455 cm$^3$ | 5.9 min |
| UHP | 20 g | 10 g | 0.368 g | 2970 cm$^3$ | 6.1 min |

EXAMPLE 10

1.0 g urea hydrogen peroxide adduct was added to dispersions of 10 mol % (relative to UHP) $Fe_{1.5}Co_{1.5}O_4$ in 0.5 g of different ionic liquids contained in glass flasks. The ionic liquids used are listed below. The flasks were closed, and the oxygen volume released by the decomposition reactions were measured with a drum gas meter. The results are shown in FIG. 12.

Figure 12:
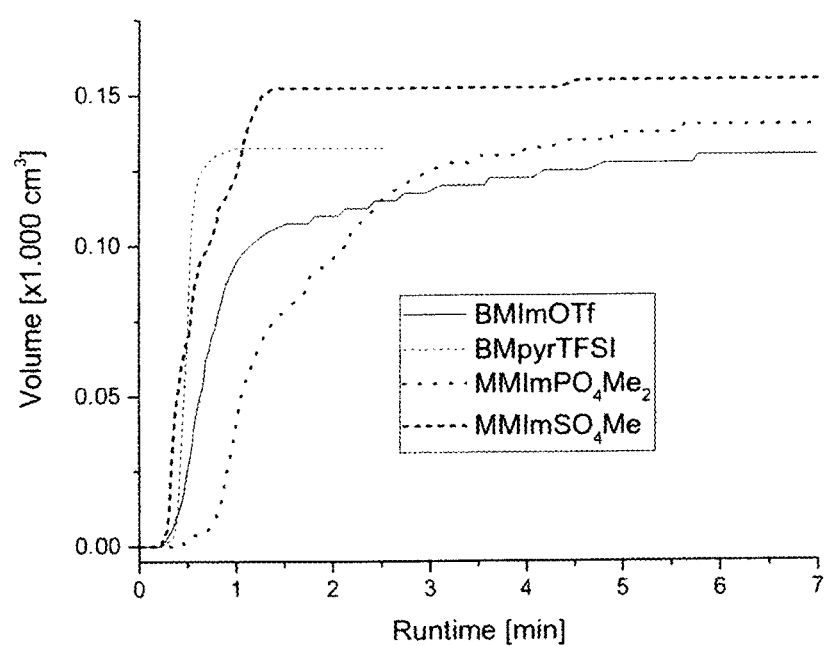
FIG. 12 illustrates oxygen release from 1 g UHP in different ionic liquids by catalytic amounts of manganese (IV) dioxide.

FIG. 12 reveals that all ionic liquids worked well. The reaction velocity was influenced to some extent by the particular ionic liquid used.

Used Ionic Liquids:
1-butyl-3-methylimidazoliumtrifluoromethanesulfonate (BMImOTf)
1,1-butylmethylpyrrolidiniumbis(trifluoromethylsulfonyl)imide (BMpyrTFSI)
1,3-dimethylimidazoliumdimethylphosphate ($MMImPO_4Me_2$)
1,3-dimethylimidazoliummethylsulfate ($MMImSO_4Me$)

EXAMPLE 11

2 g urea hydrogen peroxide adduct (UHP) were added to dispersions of different amounts of NiCo2O4 catalyst and CoFe2O2 catalyst, respectively, in 1 g $MMImPO_4Me_2$ in a glass flask. Amounts and concentrations (relative to UHP) of the catalysts are indicated in table 8. The flasks were closed, and the oxygen volume released by the decomposition reaction was measured with a drum gas meter. The reaction profiles for NiCo2O4 are shown in FIG. 13, and the reaction profiles for CoFe2O4 are shown in FIG. 14.

Figure 13:
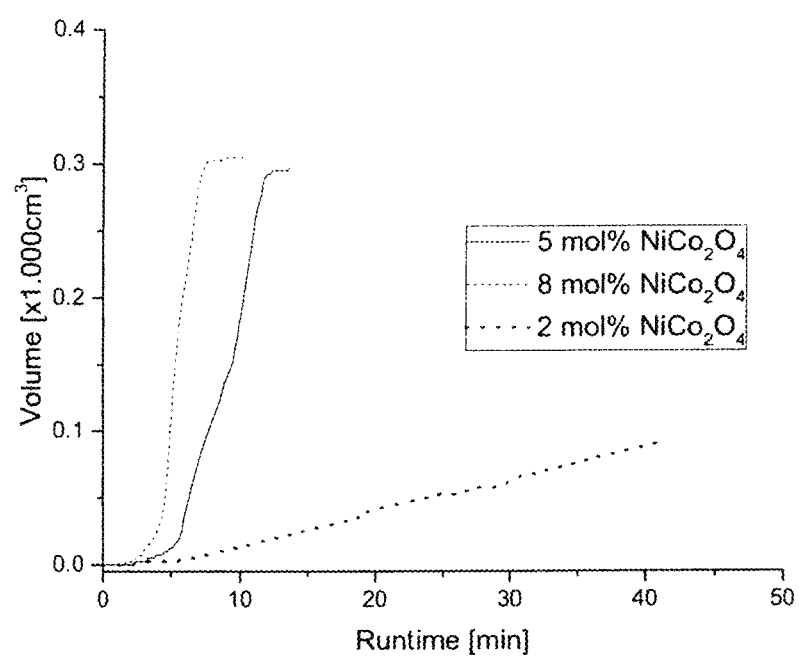
FIGS. 13 and 14 are graphs illustrating oxygen release from 2 g UHP using different catalysts and different concentrations.
Figure 14:
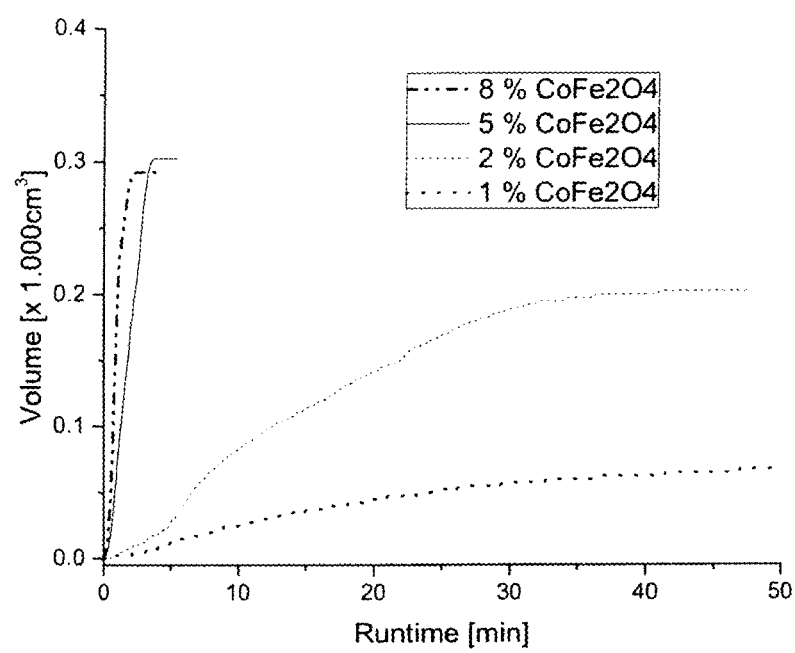

It is evident from FIGS. 13 and 14 that the catalyst concentration can be varied over a broad range and exerts a strong influence both on the reaction velocity and on the amount of oxygen released. The reaction velocity dramatically increases with increasing catalyst concentration.

TABLE 8

| peroxide adduct | catalyst | concentration catalyst | mass catalyst | volume | time |
|---|---|---|---|---|---|
| UHP | $NiCo_2O_4$ | 2 mol % | 0.152 g | 92 cm³ | 41.1 min |
| UHP | $NiCo_2O_4$ | 5 mol % | 0.382 g | 290 cm³ | 12.5 min |
| UHP | $NiCo_2O_4$ | 8 mol % | 0.612 g | 305 cm³ | 9.1 min |
| UHP | $CoFe_2O_4$ | 1 mol % | 0.050 g | 67 cm³ | 47.6 min |
| UHP | $CoFe_2O_4$ | 2 mol % | 0.100 g | 203 cm³ | 41.5 min |
| UHP | $CoFe_2O_4$ | 5 mol % | 0.250 g | 303 cm³ | 3.9 min |
| UHP | $CoFe_2O_4$ | 8 mol % | 0.399 g | 293 cm³ | 2.3 min |

EXAMPLE 12

Urea hydrogen peroxide adduct (UHP), sodium percarbonate (SPC), and mixtures thereof in the amounts listed in table 9 were added to dispersions of 0.505 g $Co_2FeO_4$ in 5 g $MMImPO_4Me_2$. The reaction vessels were closed, and the oxygen volume released by the decomposition reactions were measured with a drum gas meter. Amounts of oxygen generated as well as the reaction times are shown in FIG. 15.

TABLE 9

| mass UHP | mass SPC | volume | time |
|---|---|---|---|
| 2 g | 0 | 260 cm³ | 5.9 min |
| 1.3 g | 1.0 g | 275 cm³ | 6.2 min |
| 0 | 2 g | 265 cm³ | 7.6 min |

Figure 15:
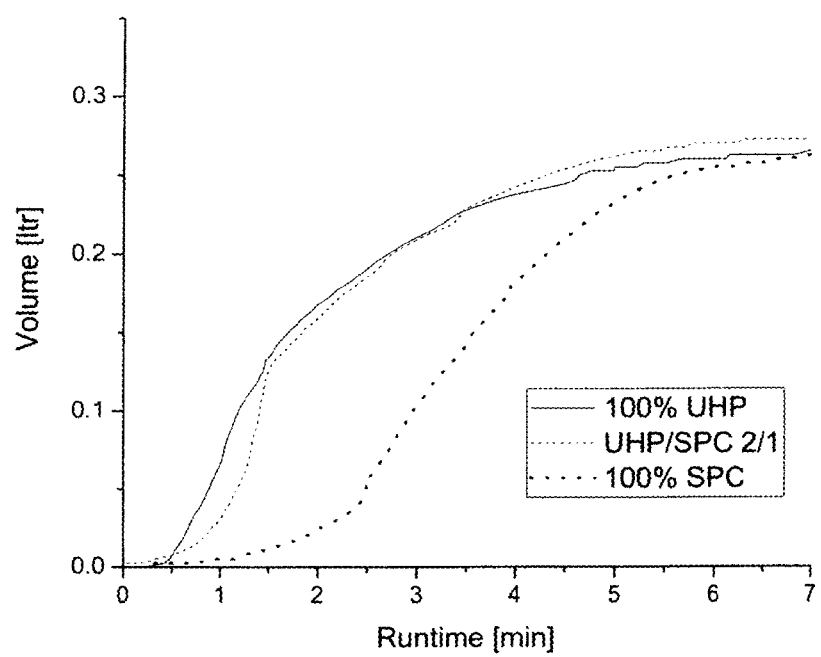
FIG. 15 illustrates oxygen release from UHP, SPC and mixtures thereof through Co2FeO4 in MMimPO4Me2.

FIG. 15 illustrates the nature of the peroxide compound has only little influence on the course of the decomposition reaction.

EXAMPLE 13

In a first experiment, 10 g urea hydrogen peroxide adduct (UHP) in powder form were added to a dispersion of 0.184 g MnO2 in 5.0 g MMImPO4Me2 contained in a glass flask.

In a second experiment, 10 g of the same UHP powder which was used in example 1, were pressed into a powder compact by applying a compaction pressure of 38 MPa. The pellet was added to a dispersion of MnO2 in MMImPO4Me2, as used in experiment 1.

Figure 16:
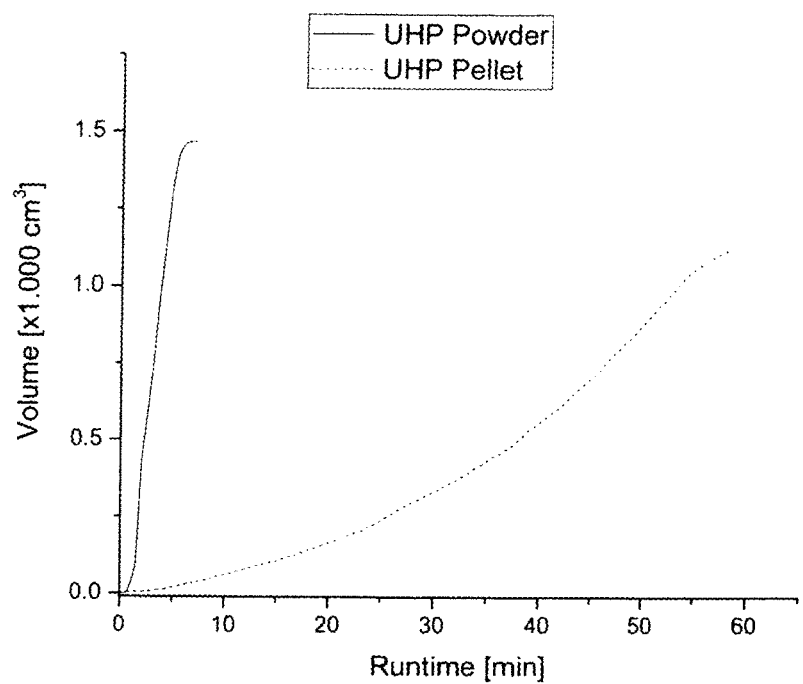
FIG. 16 illustrates oxygen release from 1 g UHP powder and 1 g UHP powder compact.

The flasks were closed, and the oxygen volumes released by the decomposition reactions were measured with a drum gas meter. The results are shown in table 10 and FIG. 16.

It is obvious that the reaction velocity was considerably reduced and the time of oxygen production considerably extended, respectively, by compacting the hydrogen peroxide adduct compound.

TABLE 10

| peroxide adduct (form) | mass | compaction pressure | volume | time |
|---|---|---|---|---|
| UHP (powder) | 10 g | — | 1460 cm³ | 7 min |
| UHP (powder compact) | 10 g | 38 MPa | 1120 cm³ | 58 min |

EXAMPLE 14

In a first experiment 2 g urea hydrogen peroxide adduct (UHP) in powder form were added to a dispersion of 0.074 g Co1.5Fe1.5O4 in 1.0 g MMImPO4Me2 contained in a glass flask.

In a second experiment, 2 g of the same UHP powder which was used in the first experiment, were pressed into a powder compact by applying a compaction pressure of 38 MPa. The pellet was added to a dispersion of Co1.5Fe1.5O4 in MMImPO4Me2 as used in experiment 1.

In a third experiment, 2 g of the same UHP powder which was used in the first and the second experiment, were pressed into a powder compact by applying a compaction pressure of 220 MPa. The pellet was added to a dispersion of Co1.5Fe1.5O4 in MMimPO4Me2 as used in experiments 1 and 2.

Figure 17:
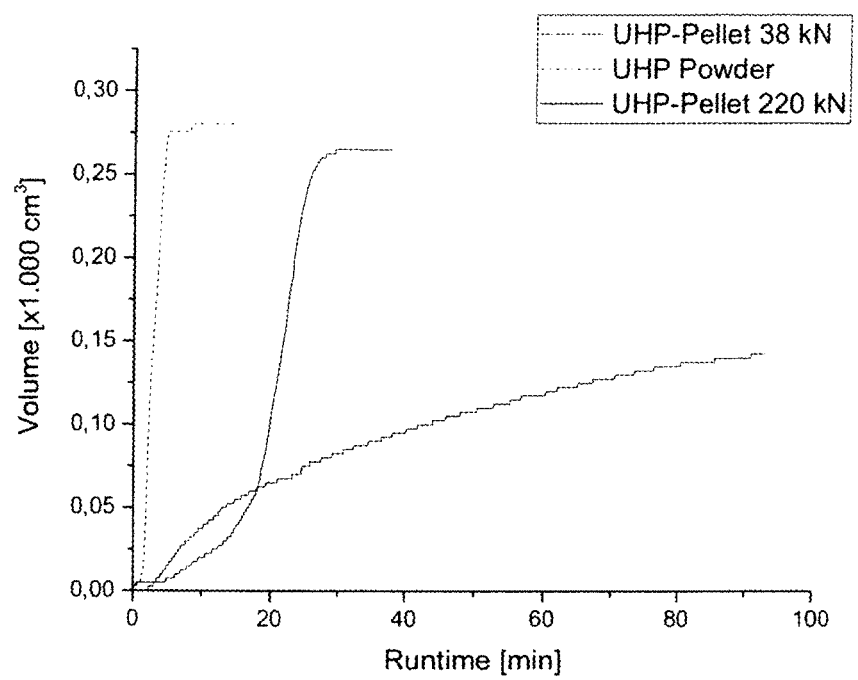
FIG. 17 illustrates oxygen release from 2 g UHP powder and two different 2 g UHP powder compacts, and FIGS. 18 to 22 schematically illustrate several embodiments of devices for generating oxygen from compositions according to the invention.

The flask was closed, and the oxygen volume released by the decomposition reactions was measured with a drum gas meter. The results are shown in table 11 and FIG. 17. It is obvious that the reaction velocity was considerably reduced and the time of oxygen generation was considerably extended, respectively, by compacting the hydrogen peroxide adduct compound into pellet form. The effect increases with increasing compaction pressure.

TABLE 11

| peroxide adduct (form) | mass | compaction pressure | mass $Co_{1.5}Fe_{1.5}O_4$ | volume | time |
|---|---|---|---|---|---|
| UHP (powder) | 2 g | — | 0.074 g | 280 cm³ | 7 min |
| UHP (powder compact) | 2 g | 38 MPa | 0.074 g | 263 cm³ | 29 min |
| UHP (powder compact) | 2 g | 220 MPa | 0.074 g | 142 cm³ | 90 min |

Thus, examples 13 and 14 prove that reducing the accessible surface area of the peroxide compound, for example by pressing, constitutes a simple measure for extending the time of oxygen release, i.e. for extending the time span wherein breathable oxygen is available.

An exemplary device for generating oxygen from compositions as described above which use ionic liquids for dissolving or dispersing a hydrogen peroxide adduct compound as an oxygen source, and for dispersing a catalyst and bringing the catalyst into contact with the oxygen source, is specifically designed. An exemplary device for generating oxygen has at least one reaction chamber for storing the composition in a condition where not all constituents of the composition are in physical contact. Such physical contact of all constituents of the composition is established at the very moment when oxygen is required. The device is equipped with suitable means for allowing the constituents to contact each other at that very moment. Furthermore, the device allows that the generated oxygen exits the reaction chamber. Some exemplary devices are illustrated in FIGS. 18 to 22, wherein like reference numerals designate like components. The description of such exemplary embodiments shall not be construed as limiting the invention in any manner.

Figure 18:
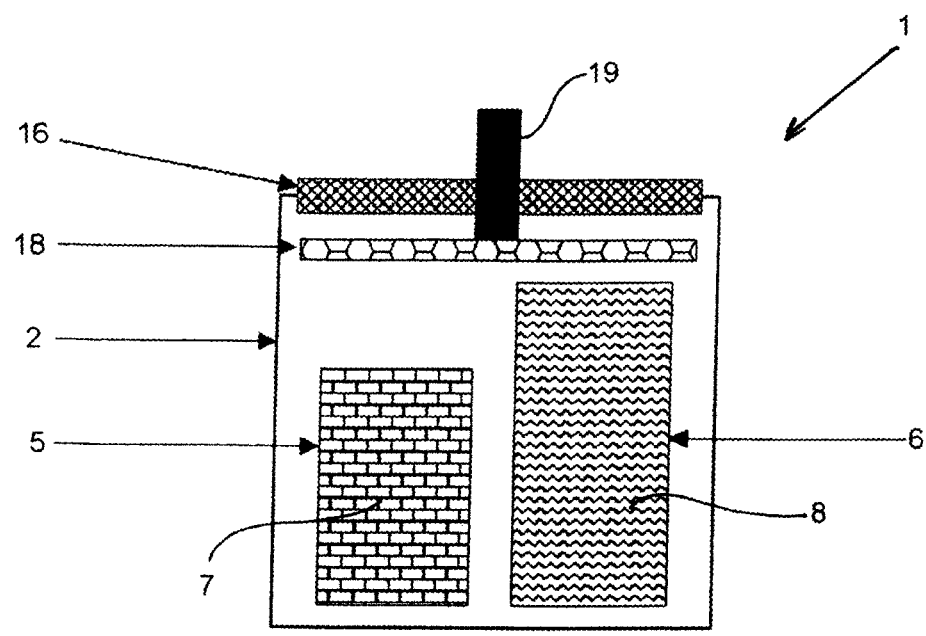

FIG. 18 illustrates a device for generating oxygen 1 having one single reaction chamber 2 for storing the composition for generating oxygen. In such a single reaction chamber 2 at least one of the constituents of the composition for generating oxygen must be enclosed in a receptacle in order to avoid contact with the remaining constituents of the composition contained in the reaction chamber 2. In the embodiment shown in FIG. 18, two receptacles 5, 6 are arranged in the reaction chamber. Receptacle 5 contains an intimate mixture of the oxygen source 7 and the decomposition catalyst 9, for example in powder form or compressed into pellets, in a thoroughly dried condition. Receptacle 6 contains the ionic liquid 8. Alternatively, there may be only one receptacle for enclosing the peroxide/catalyst mixture, while the ionic liquid is "free" within reaction chamber 2, or ionic liquid 8 may be enclosed within a receptacle, while the peroxide/catalyst mixture is not enclosed in a separate receptacle. It is, in principle, also possible to enclose only the catalyst within a separate receptacle, while the ionic liquid and the peroxide are not enclosed. It is only necessary to avoid contact between all three constituents during storage of the device for generating oxygen.

It is desirable to store the peroxide 7, the ionic liquid 8 and the catalyst 9 within the reaction chamber 2 in such an arrangement that all constituents will be able to get intimately mixed once oxygen generation is required. When, for example, the catalyst and the ionic liquid are provided in one receptacle, and the peroxide in another receptacle, the catalyst may settle within the ionic liquid during storage, and proper mixing with the peroxide may be inhibited. Quick and perfect mixing of all constituents can be achieved when the peroxide and the catalyst are intimately mixed in advance in a dry condition, optionally compacted into moulds, and filled either into the reaction chamber 2 or into a separate receptacle 5 to be placed within the reaction chamber 2, and the ionic liquid is provided in a separate receptacle 6. Placing the ionic liquid in a separate receptacle, although this is not absolutely necessary in a case where peroxide and catalyst are placed in a receptacle 5, constitutes an advantageous precautionary measure against accidental mixing of the constituents in case of receptacle 5 leakage or breakage. Care must be taken, when UHP and catalyst are mixed, because UHP is highly hygroscopic.

In a situation where oxygen shall be generated, receptacle 5, or receptacles 5 and 6, respectively, are destroyed by a breaking device 18. In FIG. 18, breaking device 18 has the form of a plate, however, means for destroying the receptacle(s) are not limited to plates, and other means are known to persons skilled in the art, for example firing pins or grids. Movement of plate 18 can be achieved by a spring 19 or another activation mechanism. During storage of the device for generating oxygen, spring 19 is under tension and holds plate 18 at a position distant from receptacles 5, 6. Once the tension is released by a suitable trigger mechanism (not shown), spring 19 moves plate 18 towards receptacles 5, 6, and plate 18 destroys receptacles 5, 6. Such a trigger may be, for example, pulling an oxygen mask towards a passenger in an airplane. Another exemplary trigger mechanism is an oxygen sensor sensing a low oxygen condition.

Receptacles 5, 6, and plate 18 are made from materials which guarantee that receptacles 5, 6 will be broken or ruptured when hit by plate 18. Exemplary materials are plastic foils or glass for receptacles 5,6, and thicker plastic material or metal for plate 18.

Destruction of receptacles 5, 6 causes mixing of peroxide, ionic liquid, and catalyst, and initiates oxygen generation. In order to allow that the oxygen exits reaction chamber 2, reaction chamber 2 has an opening. In the illustrated embodiment, the opening is sealed with a gas permeable membrane 16. The opening may be at a different position than shown in FIG. 18, or there may be more than one opening. This applies analogously to all devices for generating oxygen of the invention.

The oxygen generated in the devices of this invention may be passed through a filter or other purification means as known in the art. The devices may be equipped with such means.

The oxygen generating reaction is an only slightly exothermic process, and proceeds at low temperature, i.e. well below 150° C. Therefore, reaction chamber 2 does not need to resist high temperatures, and may be made from lightweight, low melting materials such as plastic. In addition, any bulky insulation is not required. This is particularly advantageous in all cases where weight must be saved and/or space is limited, for example in the case of oxygen masks which shall be installed in an aircraft.

Figure 19:
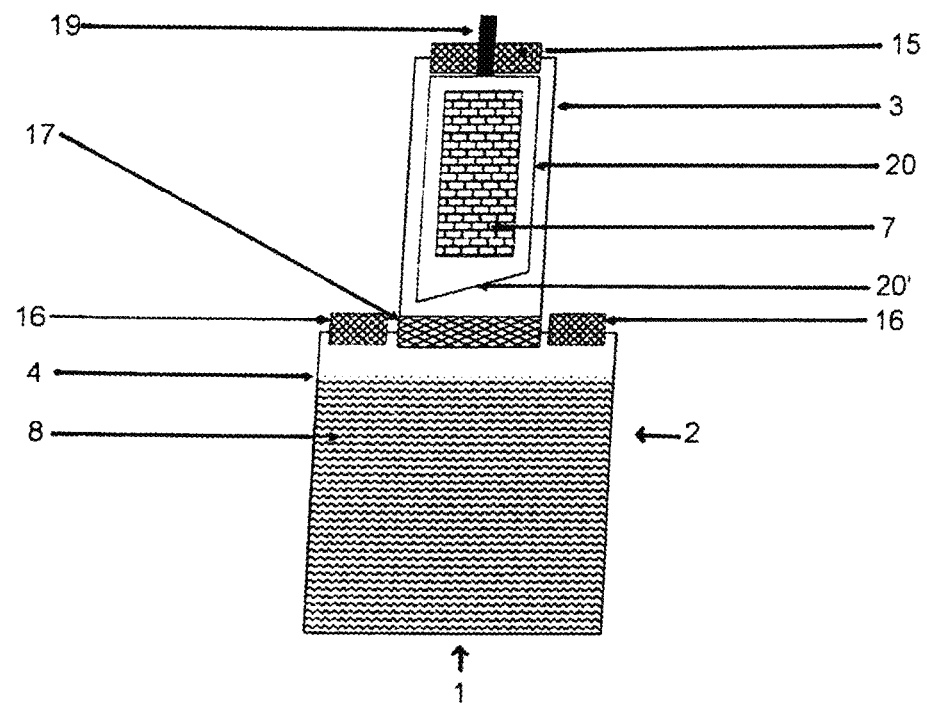

FIG. 19 illustrates an alternative embodiment of an exemplary device 1 for generating oxygen. In the embodiment of FIG. 19, the reaction chamber 2 has two compartments, a first compartment 3, and a second compartment 4, which are separated by a gastight membrane 17. The first compartment 3 contains one or more constituents of the composition for generating oxygen. Compartment 3 is equipped with a cutting device 20 having cutting edge 20', and the cutting device is arranged in a position that allows cutting edge 20' to cut through membrane 17 separating the first compartment 3 and the second compartment 4.

Compartments 3, 4 have openings sealed by membranes 15 and 16, respectively. Membranes 15, 16 are gas permeable, thus allowing the oxygen generated during the oxygen generating reaction to exit reaction chamber 2.

An activation mechanism 19, for example a spring, is provided for moving cutting device 20 towards membrane 17, and through membrane 17. Such a mechanism is described in DE 10 2009 041 065 A1. As explained in connection with FIG. 18, spring 19 is under tension during storage of device 1, and once the tension is released by a trigger mechanism (not shown), spring 19 moves receptacle 5 towards membrane 17, cutting edge 20' destroys membrane 17, and first compartment 3 and second compartment 4 are combined into one single reaction chamber 2.

In the embodiment illustrated in FIG. 19, a mixture of peroxide 7 and catalyst 9 is contained in the first compartment 3, and ionic liquid 8 is contained in second compartment 4. Upon destruction of membrane 17, the peroxide/catalyst formulation falls into the second compartment 4, and mixes with ionic liquid 8. The oxygen generated exits the reaction chamber 2 through membranes 15, 16.

Of course, it is also possible to place ionic liquid 8 into the first compartment 3 and the peroxide/catalyst formulation into the second compartment 4, or to use any other arrangement wherein at least one of the constituents is separated from the remaining constituents.

As a material for the cutting device 20, any material may be used which may cut membrane 17, for example a metal sheet. The first compartment 3 and the second compartment 4 can be formed from the same materials as the single reaction chamber 2 illustrated in FIG. 18.

Figure 20:
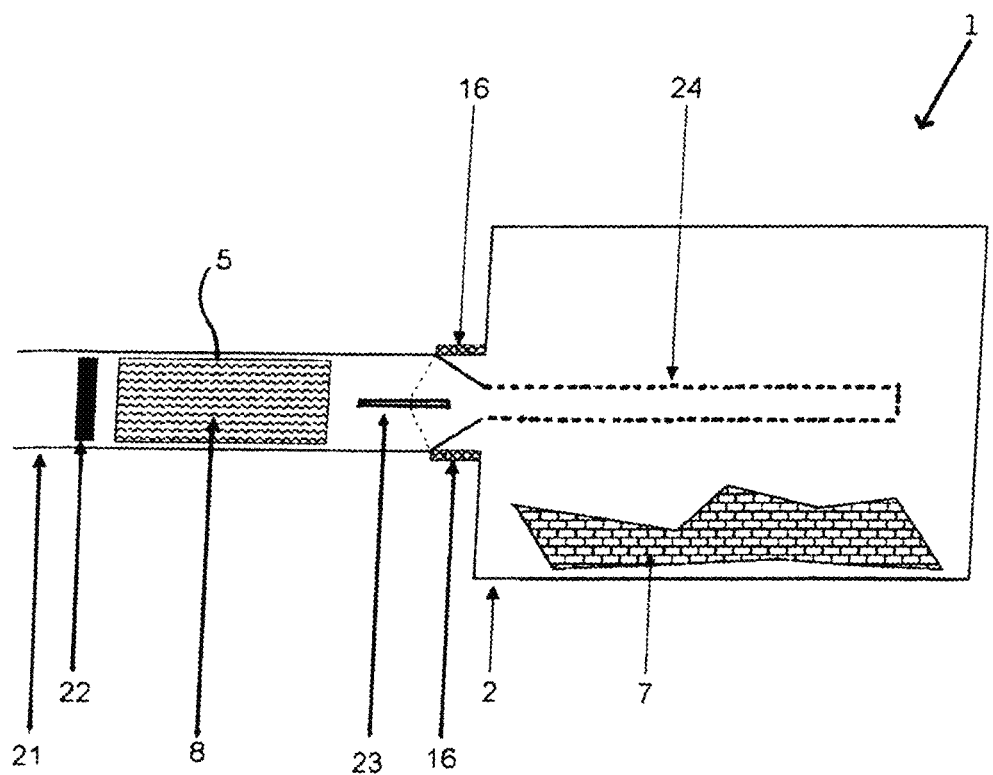

Another embodiment of an inventive device 1 for generating oxygen is illustrated in FIG. 20. In the embodiment of FIG. 20, the reaction chamber 2 is equipped with an injection device 21, for example a syringe or another dosing device.

Reaction chamber 2 and injection device 21 are connected, or constitute separate units which can be connected, to form one single unit. An opening, or several openings, in the wall of reaction chamber 2 allow that oxygen generated during the peroxide decomposition reaction exits reaction chamber 2. The openings are sealed in the embodiment shown by gas permeable membranes 16. In the embodiment illustrated in FIG. 20, the openings are provided at the junction of reaction chamber 2 and injection device 21.

The exemplary injection device of FIG. 20 comprises a slide bar 22, a spike 23, and an injection lance 24. The injection device is adapted for holding one or several constituents of the composition for generating oxygen, in the illustrated example the ionic liquid 8. Ionic liquid 8 is contained in a receptacle 5 made from a material which can be easily ruptured, for example a plastic foil. A mixture of peroxide 7 and catalyst 9 is contained in reaction chamber 2. Alternatively, catalyst 9 may be contained in ionic liquid 8. In a device as illustrated in FIG. 20, any settlement of the catalyst within the ionic liquid during storage does not constitute a disadvantage because the catalyst will be re-dispersed during the injection step.

Slide bar 22 can be actuated in an analogous manner as the breaking device 18 in FIG. 18, and the cutting device 20 in FIG. 19. Once actuated, slide bar 22 pushes receptacle 5 towards spike 23, receptacle 5 is ruptured, and ionic liquid 8 is injected through injection lance 24 into reaction chamber 2. Preferably, injection lance 24 is provided with several holes (not shown) in order to provide uniform distribution of ionic liquid 8. Ionic liquid 8 soaks the mixture of peroxide 7 and catalyst 9, or alternatively the mixture of ionic liquid 8 and catalyst 9 soaks peroxide 7, and the peroxide decomposition reaction starts, generating oxygen. The oxygen leaves reaction chamber 2 via membranes 16.

Analogously to the embodiments described above, the arrangement of peroxide 7, ionic liquid 8, and metal oxide catalyst 9 may be different from the arrangement illustrated in FIG. 20. In particular, if not a liquid, but solid matter is contained in the injection device or dosing unit 21, no receptacle 5 is required, and means for destroying the receptacle, such as spike 23, and an injection lance are also not required.

Figure 21:
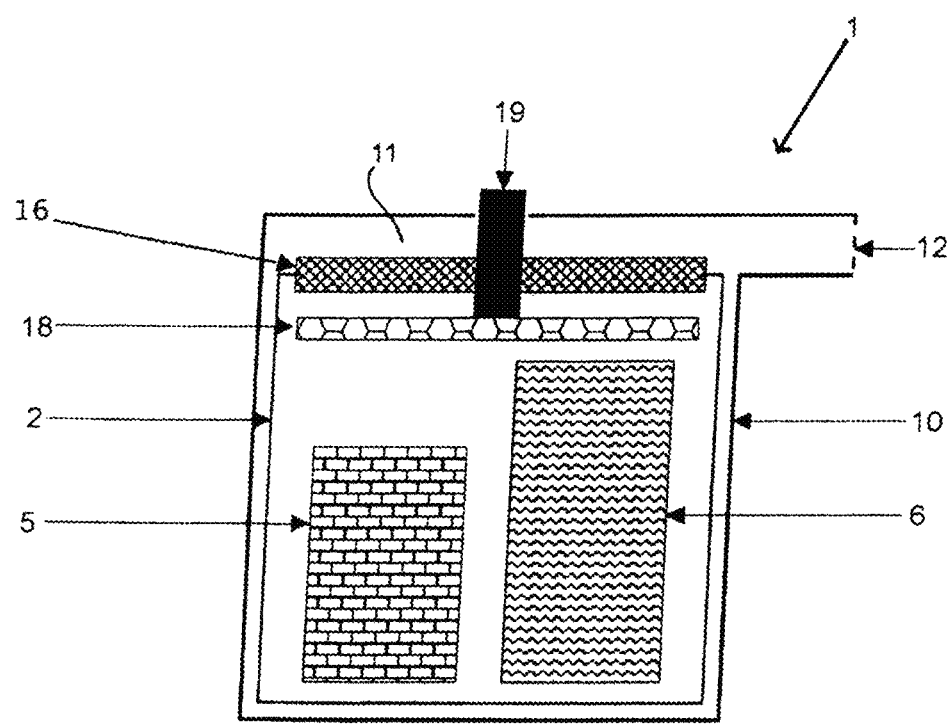

FIG. 21 depicts an embodiment of the device 1 for generating oxygen which is similar to the embodiment depicted in FIG. 18. Different from the embodiment of FIG. 18, the device for generating oxygen of FIG. 21 is contained in a container 10 surrounding and protecting reaction chamber 2. In this case, the oxygen generated is not directly released into the environment, but rather enters into a gas space 11 between gas permeable membrane 16 and an upper wall of container 10. The oxygen exits gas space 11 via a gas outlet 12 which may be, for example, provided with a filter.

A device 1 as shown in FIG. 21 typically does not need any further thermal insulation. Rather, container 10 provides for sufficient insulation. If desired, a thin layer (for example, having a thickness of about 1 to 3 mm) of an insulating material may be placed between the outer wall of reaction chamber 2 and the inner wall of container 10. Such an insulating material may also serve the additional purpose of holding reaction chamber 2 tightly fixed in place within container 10. No insulating material should be provided between membrane 16 and the container wall opposite to membrane 16, i.e. in gas space 11.

Housing the reaction chamber within a container is advantageous both in devices for generating oxygen having only one reaction chamber, and in devices for generating oxygen having more than one reaction chamber, for example two reaction chambers or a plurality or multitude of reaction chambers 2. An embodiment having eight reaction chambers 2 is illustrated in FIG. 22.

Figure 22:
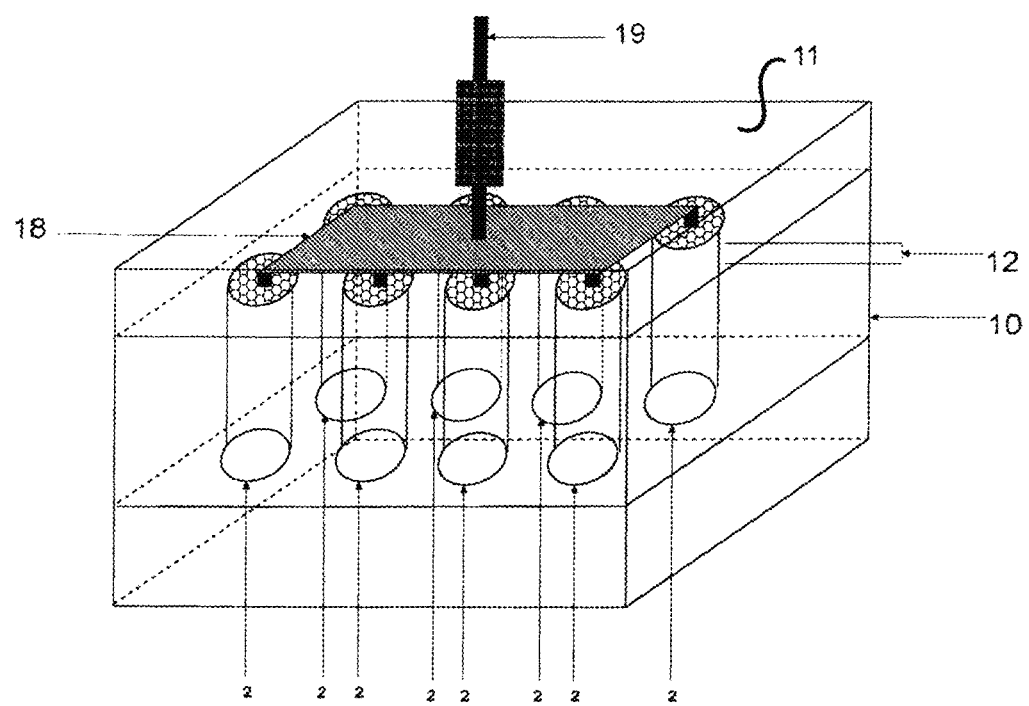

In the device for generating oxygen illustrated in FIG. 22, reaction chambers 2 are shown schematically. Generally, the construction of reaction chambers 2 is not limited in any manner. For example, reaction chambers as illustrated in FIGS. 18 to 20 can be used. Furthermore, the arrangement of the reaction chambers is not limited to the arrangement shown in FIG. 22. Rather, the reaction chambers may be arranged within the container 10 in any appropriate manner.

Oxygen generation within reaction chambers 2 is initiated upon activation of reaction chambers 2. In the embodiment shown in FIG. 22, all reaction chambers 2 are activated simultaneously by a common activation mechanism 19, such as a spring, designed for pushing a plate 18 towards reaction chambers 2, as described in connection with FIG. 18. Alternatively, each reaction chamber may be activated individually, i.e. may have its own activation mechanism, or several reaction chambers may be arranged to groups, each group having its own activation mechanism. For example, in the embodiment of FIG. 22, the eight reaction chambers might be arranged into two groups of four chambers, each group having its own activation mechanism.

Container 10 provides a gas space 11 receiving oxygen from all reaction chambers 2, and the oxygen collected within gas space 11 exits gas space 11 via gas outlet 12. Alternatively, gas space 11 may be divided into a plurality of compartments. A separate compartment, having its own gas outlet, may be attributed to each reaction chamber 2, or one compartment may provide a common gas space for a group of reaction chambers 2. For example, container 10 may provide two gas spaces 11, and each gas space 11 may collect oxygen from four reaction chambers 2.

A device for generating oxygen having several reaction chambers 2 allows to extend oxygen generation over a long time span. As explained above, the reaction time of the peroxide decomposition reaction as well as the onset of the decomposition reaction can be manipulated by choosing appropriate metal oxide catalysts, by varying catalyst amounts and, in particular, by minimizing or maximizing the accessible surface area of the peroxide compound, for example by milling the peroxide compound to a fine powder or by pressing the peroxide compound into powder compacts. The higher the compacting pressure, the higher the density of the resulting powder compacts will be, thus minimizing the accessible surface area of the peroxide compound.

In a device as illustrated in FIG. 22, each of the eight reaction chambers 2 may be charged with a different composition for generating oxygen. A first chamber may be charged for example, with a composition comprising the peroxide compound in fine powdered form, and a high catalyst concentration. This chamber will generate oxygen immediately upon activation, and with a high reaction rate. Thus, breathable oxygen will be available immediately, but only for a short time span.

Three further reaction chambers 2 may be charged also with peroxide compound in fine powdered form, and with catalyst concentrations decreasing from chamber to chamber. In these reaction chambers oxygen generation will be slower, thus extending the time span wherein breathable oxygen is available.

The remaining four reaction chambers may be charged with peroxide compound which has been pressed into powder compacts, the compacting pressure increasing from chamber to chamber. In these chambers, the onset of the decomposition reaction will be delayed, the delay increasing with increasing compaction pressure. This measure further extends the time span wherein breathable oxygen is available.

A similar result can be achieved with only one reaction chamber 2 by charging the single reaction chamber with different oxygen generating compositions, for example with different metal oxide catalysts and/or with oxygen sources in powder form and/or compressed with different compacting pressures.

Since the decomposition reactions are scalable to different reactor sizes, it is easily possible to charge an oxygen generating device with an oxygen generating composition in a sufficient amount to provide for the desired oxygen flow rate. For emergency systems it is generally desired to produce at least 4 l oxygen per minute.

Of course, also different numbers of reaction chambers than those disclosed by way of example can be advantageously used.

The devices for generating oxygen may be designed as disposable devices (single use) filled with a composition for generating oxygen or compositions for generating oxygen, respectively, or as reusable devices which can be recharged after use with another composition for generating oxygen. Therefore, the constituents of the compositions for generating oxygen can be provided in the form of components suitable for recharging a device for generating oxygen, for example in cartridges.

In an exemplary embodiment, one component comprises a metal oxide compound formulation and an ionic liquid formulation, and another component comprise an oxygen source formulation.

In another exemplary embodiment one component comprises an oxygen source formulation and a metal oxide compound formulation, and another component comprises an ionic liquid formulation.

In a further exemplary embodiment, one component comprises an oxygen source formulation, another component comprises an ionic liquid formulation, and still another component comprises a metal oxide compound formulation.

The term "oxygen source formulation" means that the oxygen source may be one single peroxide compound, but may be as well a combination of two or more peroxide compounds, and may optionally contain any additives not detrimentally interacting with the peroxide decomposition reaction.

The term "ionic liquid formulation" means that the ionic liquid may be one single ionic liquid, but may be as well a combination of two or more ionic liquids, and may optionally contain any additives not detrimentally interacting with the peroxide decomposition reaction. The ionic liquids themselves shall not react with any of the constituents of the compositions for generating oxygen, or with any intermediate products generated during the decomposition reaction.

The term "metal oxide compound formulation" means that the catalyst may be one single metal oxide compound, but may be as well a combination of two or more metal oxide compounds, and may optionally contain any additives not detrimentally interacting with the peroxide decomposition reaction.

The devices for generating oxygen according to the present invention are not sensitive to interruptions of the oxygen production process, in contrast to chlorate candles which can be easily destabilized, for example by shaking. Shaking a device for generating oxygen according to the present invention enhances mixing of the constituents of the oxygen generating composition and, therefore, promotes the oxygen generation reaction.

The inventive devices can be construed in such a manner that the orientation of the inventive devices for generating oxygen in the gravity field of the earth is arbitrary. To this end, several oxygen outlets (sealed by gas permeable membranes or other structures allowing passage of oxygen, while blocking passage of non gaseous substances) must be provided in the walls of reaction chamber(s) 2, and the openings must be arranged in such a manner, that there is always an opening which is not covered by ionic liquid, irrespective of the orientation of the device.

The invention claimed is:

1. A method for generating oxygen comprising
providing at least one oxygen source,
providing at least one ionic liquid,
providing at least one metal oxide compound, wherein
the oxygen source is a peroxide compound,
the ionic liquid is in the liquid state at least in the temperature range from −10° C. to +50° C., and
the metal oxide compound is an oxide of one single metal or of two or more different metals, said metal(s) being selected from the metals of groups 2 to 14 of the periodic table of the elements, and
contacting the oxygen source, the ionic liquid, and the metal oxide compound to generate breathable oxygen suitable for human breathing.

2. The method according to claim 1, wherein the oxygen source and the ionic liquid are provided as a first component, the metal oxide compound is provided as a second component, and the step of contacting comprises mixing the first and the second components.

3. The method according to claim 1, wherein the metal oxide compound and the ionic liquid are provided as a first component, the oxygen source is provided as a second component, and the step of contacting comprises mixing the first and the second component.

4. The method according to claim 1, wherein the oxygen source and the metal oxide compound are provided as a first component, the ionic liquid is provided as a second component, and the step of contacting comprises mixing the first and the second components.

5. The method according to claim 1, wherein the oxygen source is selected from alkali metal percarbonates, alkali metal perborates, urea hydrogen peroxide, and mixtures thereof.

6. The method according to claim 1, wherein the ionic liquid is at least one salt having a cation and an anion,
wherein the cation is selected from the group consisting of imidazolium, pyrrolidinium, ammonium, choline, pyridinium, pyrazolium, piperidinium, phosphonium, and sulfonium cations, and wherein the cation may have at least one substituent, or
wherein the ionic liquid is at least one salt having a cation and an anion, wherein the anion is selected from the group consisting of dimethylphosphate, methylsulfate, trifluoromethylsulfonate, bis(trifluoromethylsulfonyl) imide, chloride, bromide, iodide, tetrafluoroborate, and hexafluorophosphate.

7. The method according to claim 1, wherein the ionic liquid is selected from the group consisting of
butyltrimethylammoniumbis(trifluoromethylsulfonyl) imide ([Me3BuN]TFSI)
1-butyl-3-methylimidazoliumtrifluoromethanesulfonate (BMImOTf),
1-butyl-3-methylimidazoliumdimethylphosphate (BMImPO4Me2),
1-butyl-3-methylimidazoliummethylsulfate (BMImSO4Me),
1,1-butylmethylpyrrolidiniumbis(trifluoromethylsulfonyl)imide (BmpyrTFSI),
1,3-dimethylimidazoliumdimethylphosphate (MMImPO4Me2),
1,3-dimethylimidazoliummethylsulfate (MMImSO4Me).

8. The method according to claim 1, wherein the metal oxide compound is at least one oxide containing one single metal, optionally in different oxidation states.

9. The method according to claim 1, wherein the metal oxide compound is one or more of $MnO_2$, $Co_3O_4$, $CrO_3$, $Ag_2O$, $CuO$, and $PbO_2$.

10. The method according to claim 1, wherein the metal oxide compound is at least on oxide containing at least two different metals.

11. The method according to claim 1, wherein the metal oxide compound is selected from spinel type metal oxides, ilmenite type metal oxides and perovskite type metal oxides.

12. The method according to claim 1, wherein the metal oxide compound is selected from mixed cobalt iron oxides, mixed copper iron oxides, mixed nickel iron oxides, mixed manganese iron oxides, mixed copper manganese oxides, mixed cobalt manganese oxides, mixed nickel manganese oxides, mixed nickel cobalt oxides, mixed lanthanum iron nickel oxides, mixed lanthanum strontium manganese oxide, and mixtures thereof.

13. The method according to claim 1, wherein at least one of the oxygen source and the metal oxide compound is in the form of at least one powder compact, or in the form of powder compacts having different degrees of compression.

14. The method according to claim 13, wherein the at least one powder compact has been compacted with a pressure in the range of 1 to 220 MPa.

15. The method according to claim 1, wherein the oxygen source is present in an amount ranging from 10 to 80 weight %, the ionic liquid is present in an amount ranging from 20 to 80 weight %, and the metal oxide compound is present in an amount ranging from more than 0 to 20 weight %.

16. The method according to claim 5, wherein the oxygen source is selected from the group consisting of one or more of $Na_2CO_3 \times 1.5\ H_2O_2$, $NaBO_3 \times 4H_2O$, $NaBO_3 \times H_2O$, and urea hydrogen peroxide.

* * * * *